US012642892B2

(12) United States Patent
Kuramoto

(10) Patent No.: US 12,642,892 B2
(45) Date of Patent: Jun. 2, 2026

(54) MEDICAL DEVICE AND METHOD FOR MANUFACTURING SAME

(71) Applicant: TERUMO KABUSHIKI KAISHA, Tokyo (JP)

(72) Inventor: Masanori Kuramoto, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1086 days.

(21) Appl. No.: 17/675,063

(22) Filed: Feb. 18, 2022

(65) Prior Publication Data

US 2022/0176022 A1 Jun. 9, 2022

Related U.S. Application Data

(63) Continuation of application No. PCT/JP2020/031640, filed on Aug. 21, 2020.

(30) Foreign Application Priority Data

Aug. 21, 2019 (JP) ................................ 2019-151583

(51) Int. Cl.
*A61L 31/10* (2006.01)
*A61L 29/04* (2006.01)
(Continued)

(52) U.S. Cl.
CPC ............. *A61L 31/10* (2013.01); *A61L 29/041* (2013.01); *A61L 29/049* (2013.01); *A61L 29/06* (2013.01);
(Continued)

(58) Field of Classification Search
None
See application file for complete search history.

(56) References Cited

U.S. PATENT DOCUMENTS

2008/0292776 A1 11/2008 Dias et al.
2016/0015869 A1 1/2016 Omata et al.
(Continued)

FOREIGN PATENT DOCUMENTS

CN 105073155 A 11/2015
CN 109641994 * 4/2019
(Continued)

OTHER PUBLICATIONS

A. C. Drumeanu, "Polyacrylamide—New Opportunity in Lubrication", Journal of the Balkan Tribological Association, Sep. 30, 2012, vol. 18, No. 3, pp. 485-495. (13 pages). XP093109375.
(Continued)

*Primary Examiner* — Yan Lan
(74) *Attorney, Agent, or Firm* — BUCHANAN INGERSOLL & ROONEY PC

(57) ABSTRACT

A medical device includes: a substrate layer; an adhesive layer formed on at least a part of the substrate layer and containing a hydrophilic copolymer (1) containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group; and a surface lubricious layer formed on at least a part of the adhesive layer and containing a polymer containing a structural unit derived from acrylamide and a hydrophilic copolymer (2).

12 Claims, 2 Drawing Sheets

10

(51) Int. Cl.

| | |
|---|---|
| ***A61L 29/06*** | (2006.01) |
| ***A61L 29/08*** | (2006.01) |
| ***A61L 29/14*** | (2006.01) |
| ***A61L 31/04*** | (2006.01) |
| ***A61L 31/14*** | (2006.01) |
| ***C08F 220/38*** | (2006.01) |

(52) U.S. Cl.

CPC ............ *A61L 29/085* (2013.01); *A61L 29/14* (2013.01); *A61L 31/041* (2013.01); *A61L 31/14* (2013.01); *C08F 220/387* (2020.02); *A61L 2400/10* (2013.01); *A61L 2420/02* (2013.01); *A61L 2420/06* (2013.01)

(56) References Cited

U.S. PATENT DOCUMENTS

| | | | |
|---|---|---|---|
| 2016/0024240 | A1 | 1/2016 | Ochiai et al. |
| 2019/0185776 | A1 | 6/2019 | Kuramoto et al. |
| 2022/0168475 | A1 | 6/2022 | Ueno et al. |
| 2022/0168476 | A1 | 6/2022 | Kuramoto |
| 2022/0168479 | A1 | 6/2022 | Kuramoto |
| 2022/0177618 | A1 | 6/2022 | Kuramoto et al. |

FOREIGN PATENT DOCUMENTS

| | | | |
|---|---|---|---|
| CN | 109641994 | A | 4/2019 |
| EP | 3 505 543 | A1 | 7/2019 |
| EP | 4 018 975 | A1 | 6/2022 |
| JP | 2004357826 | A | 12/2004 |
| JP | 2008-119022 | A | 5/2008 |
| WO | 2007/065722 | A1 | 6/2007 |
| WO | 2010113632 | A1 | 10/2010 |
| WO | 2014204407 | A1 | 12/2014 |
| WO | 2018038063 | A1 | 3/2018 |
| WO | 2020004385 | A1 | 1/2020 |

OTHER PUBLICATIONS

Office Action (Communication pursuant to Article 94(3) EPC) issued on Jan. 26, 2024, in corresponding European Patent Application No. 20854470.0. (6 pages).

U.S. Appl. No. 17/674,891, filed Feb. 18, 2022, Masanori Kuramoto et al.

U.S. Appl. No. 17/675,334, filed Feb. 18, 2022, Masanori Kuramoto.

U.S. Appl. No. 17/675,565, filed Feb. 18, 2022, Masanori Kuramoto.

U.S. Appl. No. 17/675,343, filed Feb. 18, 2022, Yuki Ueno et al.

English Translations of the International Search Report (Form PCT/ISA/210) and the Written Opinion of the International Searching Authority (Form PCT/ISA/237) issued Sep. 29, 2020, by the Japanese Patent Office in corresponding International Application No. PCT/JP2020/031640. (5 pages).

International Search Report (PCT/ISA/210) with English translation and Written Opinion (PCT/ISA/237) mailed on Sep. 29, 2020, by the Japanese Patent Office as the International Searching Authority for International Application No. PCT/JP2020/031640.

The extended European Search Report issued Aug. 16, 2022, by the European Patent Office in corresponding European Patent Application No. 20854470.0-1107. (34 pages).

Office Action (The First Office Action) issued Feb. 3, 2023, by the National Intellectual Property Administration, P.R. China in corresponding Chinese Patent Application No. 202080058744.2 and an English translation of the Office Action. (12 pages).

* cited by examiner

FIG. 1
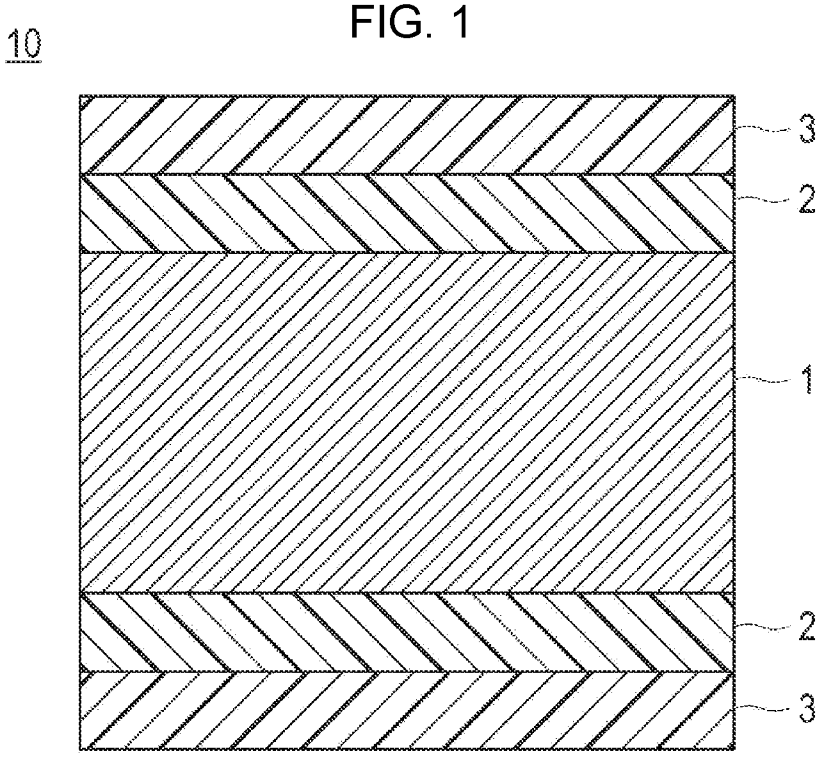
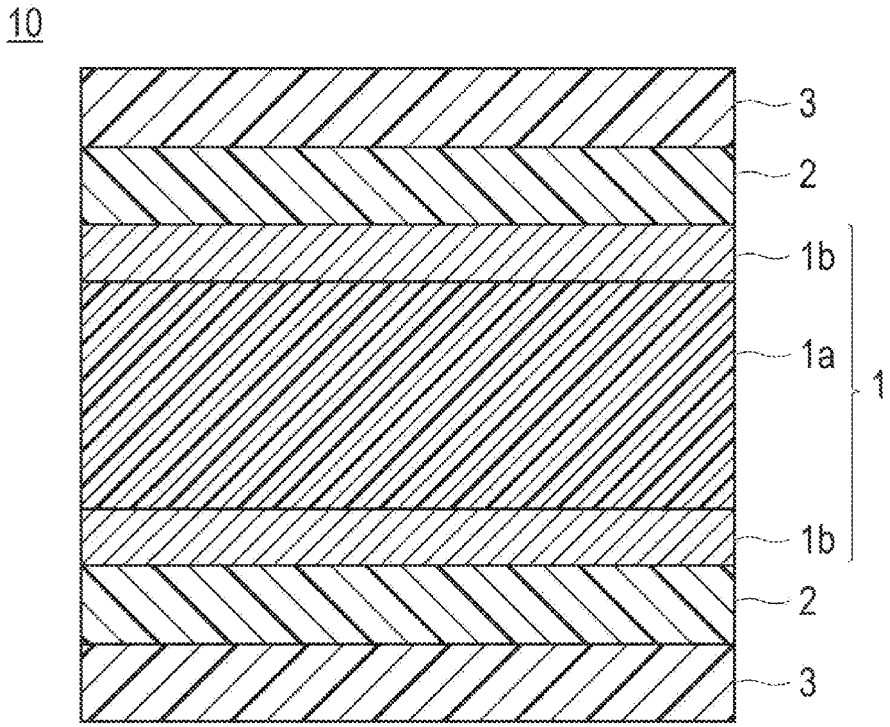
FIG. 2

FIG. 3
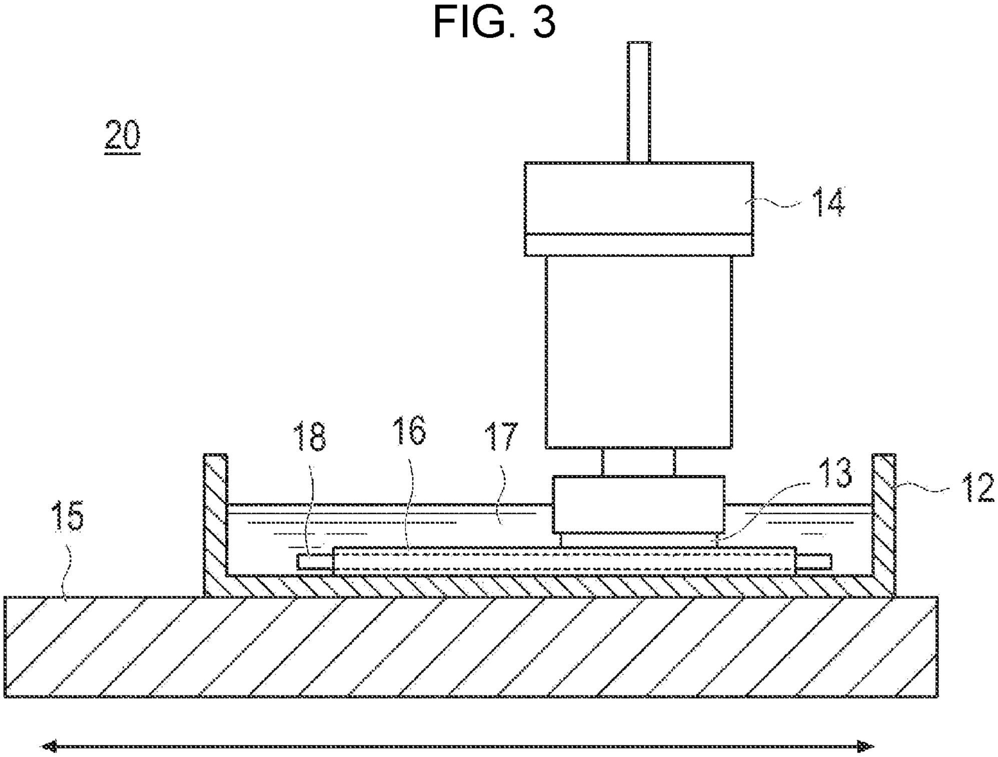
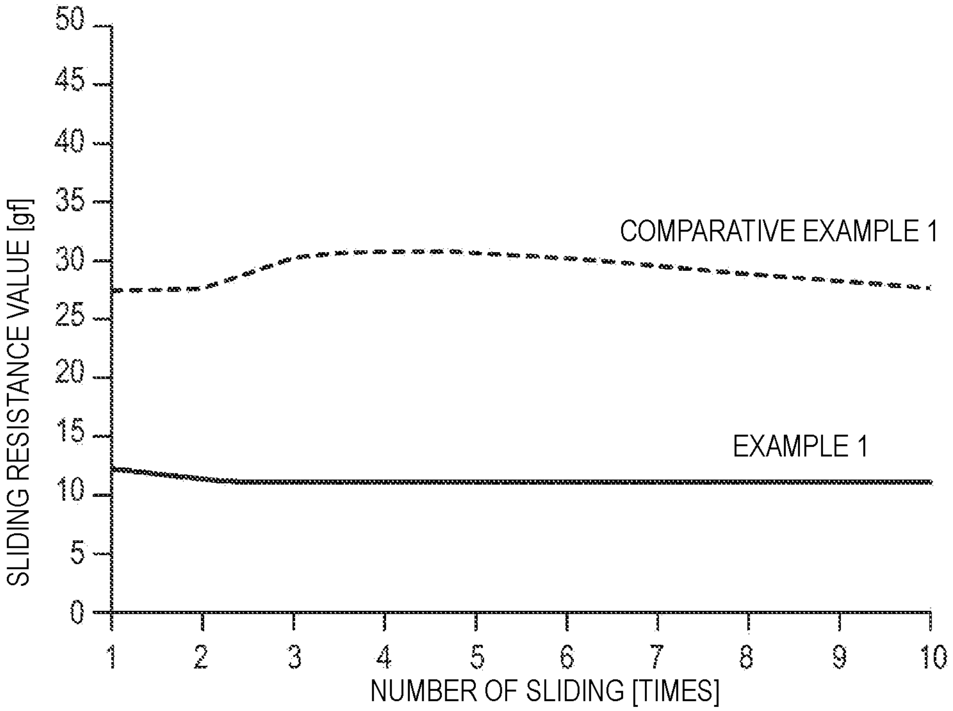
FIG. 4

MEDICAL DEVICE AND METHOD FOR MANUFACTURING SAME

CROSS-REFERENCE TO RELATED APPLICATIONS

This application is a continuation of International Patent Application No. PCT/JP2020/031640 filed on Aug. 21, 2020, which claims priority to Japanese Patent Application No. 2019-151583, filed on Aug. 21, 2019, the entire content of both of which is incorporated herein by reference.

TECHNOLOGICAL FIELD

The disclosure here relates to a medical device and a method for manufacturing the same. In particular, the disclosure relates to a medical device including a surface lubricious layer exhibiting an excellent lubricating property and a method for manufacturing the same.

BACKGROUND DISCUSSION

In recent years, a catheter with a reduced outer diameter has been used to improve insertion to a peripheral portion of a blood vessel, and is thereby used for diagnosis and treatment of various lesion sites. Therefore, in the diagnosis or the treatment using the catheter, a clearance between the catheter and an inner surface of a lumen in a living body is extremely small, which may result in high frictional resistance on a surface of the catheter. Therefore, the catheter is required to include a coating that imparts a lubricating property and durability (lubrication retaining property) to the surface of the catheter.

For example, WO 2018/038063 (corresponding to US 2019/0185776 A1) discloses that a hydrophilic copolymer is used for a surface lubricious layer, the hydrophilic copolymer containing a structural unit derived from a polymerizable monomer (A) having a sulfobetaine structure, a structural unit derived from a polymerizable monomer (B) having a group such as a sulfonic acid group, and a structural unit derived from a polymerizable monomer (C) having a photoreactive group.

SUMMARY

The surface lubricious layer disclosed in WO 2018/038063 (corresponding to US 2019/0185776 A1) certainly exhibits an excellent lubricating property and excellent durability (lubrication retaining property). On the other hand, a medical technique for advancing a more flexible medical device to a narrower lesion site in a living body becomes widespread, and in recent years, a demand for operability for making the medical device reach the lesion site increases. Therefore, a technique for further improving the lubricating property in order to operate the medical device satisfactorily even in a narrower lesion site is demanded.

The disclosure here provides a way for improving the lubricating property.

The present inventor has made diligent studies to solve the above problem. As a result, the present inventor has found that the above problem can be solved by providing, on a substrate layer, an adhesive layer containing a hydrophilic copolymer containing specific structural units and a surface lubricious layer containing a hydrophilic copolymer containing specific structural units and a polymer containing a structural unit derived from acrylamide, and has thus completed the discovery described below.

Disclosed here is a medical device including: a substrate layer; an adhesive layer formed on at least a part of the substrate layer and containing a hydrophilic copolymer (1) containing a structural unit derived from a polymerizable monomer (A) having a sulfobetaine structure, a structural unit derived from a polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C) having a photoreactive group; and a surface lubricious layer formed on at least a part of the adhesive layer and containing a polymer containing a structural unit derived from acrylamide and a hydrophilic copolymer (2) containing a structural unit derived from a polymerizable monomer (A') having a sulfobetaine structure, a structural unit derived from a polymerizable monomer (B') having at least one group selected from the group consisting of a sulfonic acid group ($—SO_3H$), a sulfuric acid group ($—OSO_3H$), a sulfurous acid group ($—OSO_2H$), and salt groups thereof, and a structural unit derived from a polymerizable monomer (C') having a photoreactive group.

Another aspect involves a method comprising inserting a medical device into a lumen in a living body. The medical device comprises a substrate layer and an adhesive layer formed on at least a part of the substrate layer. The adhesive layer contains a hydrophilic copolymer (1) containing (i) a structural unit derived from a polymerizable monomer (A) having a sulfobetaine structure, (ii) a structural unit derived from a polymerizable monomer (B) having at least one group selected from the group consisting of a sulfonic acid group, a sulfuric acid group, a sulfurous acid group, and salt groups thereof, and (iii) a structural unit derived from a polymerizable monomer (C) having a photoreactive group. The medical device further includes a surface lubricious layer formed on at least a part of the adhesive layer. The surface lubricious layer contains a polymer, said polymer containing (a) a structural unit derived from acrylamide, and (b) a hydrophilic copolymer (2) containing (i) a structural unit derived from a polymerizable monomer (A') having a sulfobetaine structure, (ii) a structural unit derived from a polymerizable monomer (B') having at least one group selected from the group consisting of a sulfonic acid group, a sulfuric acid group, a sulfurous acid group, and salt groups thereof, and (iii) a structural unit derived from a polymerizable monomer (C') having a photoreactive group. The method further involves moving the medical device in the lumen in the living body, whereby aqueous liquid in the lumen contacts and wets the surface lubricious layer so that the surface lubricious layer exhibits a lubricating property. In a yet further aspect the medical device is a catheter, a stent, or a guide wire.

A further aspect disclosed here involves a method for manufacturing a medical device comprising: applying a coating liquid (1) onto a substrate to form an adhesive layer on the substrate, and applying a coating liquid (2) onto the adhesive layer to form a surface lubricious layer. The coating liquid (1) comprises: a hydrophilic copolymer (1) containing: i) a structural unit derived from a polymerizable monomer (A) having a sulfobetaine structure; ii) a structural unit derived from a polymerizable monomer (B) having at least one group selected from the group consisting of a sulfonic acid group, a sulfuric acid group, a sulfurous acid group, and salt groups thereof; and iii) a structural unit derived from a polymerizable monomer (C) having a photoreactive group. The coating liquid (2) comprises a polymer containing: (a) a structural unit derived from acrylamide; and (b) a hydrophilic copolymer (2), the hydrophilic copolymer (2) containing: i) a structural unit derived from a polymerizable monomer (A') having a sulfobetaine structure; ii) a structural unit derived from a polymerizable monomer (B') having at least one group selected from the group consisting of a sulfonic acid group, a sulfuric acid group, a sulfurous acid group, and salt groups thereof; and iii) a structural unit derived from a polymerizable monomer (C') having a photoreactive group.

BRIEF DESCRIPTION OF THE DRAWINGS

FIG. 1 is a partial cross-sectional view schematically showing a surface lamination structure of a medical device according to an exemplary embodiment of the medical device.

FIG. 2 is a partial cross-sectional view schematically showing a configuration example having a different surface lamination structure as an application example of the embodiment in FIG. 1.

FIG. 3 is a schematic view showing a lubricating property and durability test device (friction meter) used in Examples and Comparative Examples.

FIG. 4 is a graph showing lubricating property and durability test results in Example 1 and Comparative Example 1.

DETAILED DESCRIPTION

Set forth below with reference to the accompanying drawings is a detailed description of embodiments of a medical device and manufacturing method representing examples of the inventive catheter disclosed herein. The invention is not limited to the following embodiments. In the present description, "X to Y" indicating a range includes X and Y, and means "X or more and Y or less". In the present description, "X and/or Y" means to include at least one of X and Y, and includes "X alone", "Y alone", and "a combination of X and Y". Unless otherwise specified, operations, measurements of physical properties, and the like are performed under conditions of room temperature (20° C. to 25° C.) and a relative humidity of 40% to 60% RH.

In the present description, the term "(meth)acrylic" includes both acrylic and methacrylic. Therefore, for example, the term "(meth)acrylic acid" includes both acrylic acid and methacrylic acid. Similarly, the term "(meth) acryloyl" includes both acryloyl and methacryloyl. Therefore, for example, the term "(meth)acryloyl group" includes both an acryloyl group and a methacryloyl group.

In the present description, unless otherwise specified, the term "substituted" refers to being substituted with a C1 to C30 alkyl group, a C2 to C30 alkenyl group, a C2 to C30 alkynyl group, a C1 to C30 alkoxy group, an alkoxycarbonyl group (—COOR, R represents a C1 to C30 alkyl group), a halogen atom (F, Cl, Br, or I atom), a C6 to C30 aryl group, a C6 to C30 aryloxy group, an amino group, a C1 to C30 alkylamino group, a cyano group, a nitro group, a thiol group, a C1 to C30 alkylthio group, or a hydroxy group. Note that, when a group is substituted, a substitution in which a structure after substitution falls under a definition before the substitution is excluded. For example, when a substituent is an alkyl group, this alkyl group as a substituent is not further substituted with another alkyl group.

In the present description, a "polymerizable monomer (A) having a sulfobetaine structure" is also simply referred to as a "polymerizable monomer (A)" or a "polymerizable monomer (A) according to the invention". Similarly, a "structural unit derived from a polymerizable monomer (A) having a sulfobetaine structure" is also simply referred to as a "structural unit (A)" or a "structural unit (A) according to the invention". Similarly, in the present description, a "polymerizable monomer (A') having a sulfobetaine structure" is also simply referred to as a "polymerizable monomer (A')" or a "polymerizable monomer (A') according to the invention". Similarly, a "structural unit derived from a polymerizable monomer (A') having a sulfobetaine structure" is also simply referred to as a "structural unit (A')" or a "structural unit (A') according to the invention".

In the present description, a "polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof" is also simply referred to as a "polymerizable monomer (B)" or a "polymerizable monomer (B) according to the invention". Similarly, a "structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof" is also simply referred to as a "structural unit (B)" or a "structural unit (B) according to the invention". Similarly, in the present description, a "polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof" is also simply referred to as a "polymerizable monomer (B')" or a "polymerizable monomer (B') according to the invention". Similarly, a "structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof" is also simply referred to as a "structural unit (B')" or a "structural unit (B') according to the invention".

In the present description, a "polymerizable monomer (C) having a photoreactive group" is also simply referred to as a "polymerizable monomer (C)" or a "polymerizable monomer (C) according to the invention". Similarly, a "structural unit derived from a polymerizable monomer (C) having a photoreactive group" is also simply referred to as a "structural unit (C)" or a "structural unit (C) according to the invention". Similarly, in the present description, a "polymerizable monomer (C') having a photoreactive group" is also simply referred to as a "polymerizable monomer (C')" or a "polymerizable monomer (C') according to the invention". Similarly, a "structural unit derived from a polymerizable monomer (C') having a photoreactive group" is also simply referred to as a "structural unit (C')" or a "structural unit (C') according to the invention".

In the present description, a "hydrophilic copolymer (1) containing a structural unit (A), a structural unit (B), and a structural unit (C)" is also simply referred to as a "hydrophilic copolymer (1)" or a "hydrophilic copolymer (1) according to the invention". Similarly, in the present description, a "hydrophilic copolymer (2) containing a structural unit (A'), a structural unit (B'), and a structural unit (C')" is also simply referred to as a "hydrophilic copolymer (2)" or a "hydrophilic copolymer (2) according to the invention".

In the present description, a "polymerizable monomer" is also simply referred to as a "monomer".

In the present description, a "structural unit derived from acrylamide" is also simply referred to as an "acrylamide structural unit". A "polymer containing a structural unit derived from acrylamide" is also simply referred to as an "acrylamide-based polymer".

In the present description, when a structural unit is said to be "derived" from a monomer, it means that the structural unit is a divalent structural unit generated by a polymerizable unsaturated double bond (C═C) present in the monomer corresponding to the structural unit becoming a single bond (—C—C—).

According to a first aspect, a medical device is provided, the medical device including: a substrate layer; an adhesive layer formed on at least a part of the substrate layer and containing a hydrophilic copolymer (1) containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group; and a surface lubricious layer formed on at least a part of the adhesive layer and containing a polymer containing a structural unit derived from acrylamide and a hydrophilic copolymer (2) containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group. The medical device having the above configuration can exhibit an excellent lubricating property.

In recent years, miniaturization and diameter reduction of medical devices have advanced, and a medical technique for advancing a more flexible medical device to a narrower lesion site in a living body has become widespread. A device that can maintain good operability even in a site where a clearance between the medical device and an inner surface of a lumen in the living body is small is demanded. The present inventor has made diligent studies to meet such a demand. As a result, the present inventor has found that a high lubricating property can be exhibited even under a high load condition (that is, even in a site where the clearance between the medical device and the inner surface of the lumen in the living body is small) by using the surface lubricious layer described in the above WO 2018/038063 (corresponding to US 2019/0185776 A1) as an adhesive layer and providing, on the adhesive layer, a surface lubricious layer containing a hydrophilic copolymer and a polymer containing a structural unit derived from acrylamide. A mechanism by which such an effect is produced is unclear, but the following mechanism is theorized. Note that the following mechanism is theory, and the invention is not limited to the following theory. Specifically, the surface lubricious layer contains the hydrophilic copolymer (hydrophilic copolymer (2)) and the polymer containing a structural unit derived from acrylamide. Here, the hydrophilic copolymer (hydrophilic copolymer (2)) contained in the surface lubricious layer exhibits a lubricating property when wet (for example, when in contact with an aqueous liquid such as a body fluid or physiological saline). In addition, the polymer containing a structural unit derived from acrylamide has a water retention effect (acts as a water-retaining material). In such a surface lubricious layer, in addition to a water absorption effect of the water-retaining material, a crosslink density is moderately low due to presence of the water-retaining material. Therefore, the aqueous liquid easily enters the surface lubricious layer (the hydrophilic copolymer (2) easily exhibits a lubricating property (surface gel hydration lubrication) when in contact with the aqueous liquid). Under a high load condition, the surface lubricious layer disclosed here can maintain a sufficient hydrated layer on a surface of the medical device due to the aqueous liquid retained on the surface lubricious layer. Therefore, it is considered that the hydrophilic copolymer (2) can exhibit a sufficient lubricating property even under a high load condition.

The hydrophilic copolymer (1) in the adhesive layer and the hydrophilic copolymer (2) in the surface lubricious layer each have a photoreactive group. When the adhesive layer or the surface lubricious layer is irradiated with active energy rays, the photoreactive group generates reactive species, and the hydrophilic copolymer (1) in the adhesive layer reacts with the substrate layer (resin) to form a covalent bond between the substrate layer and the adhesive layer. In addition, due to the generation of these reactive species, the hydrophilic copolymer (1) in the adhesive layer reacts with the hydrophilic copolymer (2) or the polymer containing a structural unit derived from acrylamide in the surface lubricious layer, so that a covalent bond is also formed between the adhesive layer and the surface lubricious layer. Accordingly, according to the disclosure, by providing the adhesive layer between the substrate layer and the surface lubricious layer, the surface lubricious layer can be firmly immobilized to the substrate layer via the adhesive layer. Therefore, the medical device according to the disclosure can maintain an initial lubricating property for a longer period of time and have further improved durability (lubrication retaining property).

Therefore, the medical device according to the disclosure can exhibit an excellent lubricating property even under a condition where the clearance between the medical device and the inner surface of the lumen in the living body is small (high load condition). In addition, the medical device according to the disclosure can exhibit excellent durability (lubrication retaining property).

Hereinafter, a preferred embodiment of the medical device disclosed here will be described with reference to the attached drawings.

FIG. 1 is a partial cross-sectional view schematically showing a surface lamination structure of a medical device according to an exemplary embodiment of the medical device (hereinafter, also simply referred to as a "medical device"). FIG. 2 is a partial cross-sectional view schematically showing a configuration example having a different surface lamination structure as an application example in the present embodiment. Note that in FIG. 1 and FIG. 2, 1 represents a substrate layer, 1*a* represents a substrate layer core portion, 1*b* represents a substrate surface layer, 2 represents an adhesive layer, 3 represents a surface lubricious layer, and 10 represents a medical device.

As shown in FIG. 1 and FIG. 2, the medical device 10 according to the present embodiment includes: the substrate layer 1; the adhesive layer 2 containing the hydrophilic copolymer (1) and immobilized (disposed) so as to cover at least a part of a surface of the substrate layer 1 (in the drawing, an example of being immobilized (disposed) on the whole surface (entire surface) of the substrate layer 1 in the drawing is shown); and the surface lubricious layer 3 containing the hydrophilic copolymer (2) and a polymer containing a structural unit derived from acrylamide and immobilized (disposed) so as to cover at least a part of a surface of the adhesive layer 2 (in the drawing, an example of being immobilized (disposed) on the whole surface (entire surface) of the adhesive layer 2 in the drawing is shown). The adhesive layer 2 is bonded to the substrate layer 1 and the hydrophilic copolymer (2) and the polymer containing a structural unit derived from acrylamide in the surface lubricious layer 3 via the photoreactive group of the hydrophilic copolymer (1).

Hereinafter, each configuration of the medical device according to the present embodiment will be described.

The disclosure relates to a medical device, the medical device including: a substrate layer; an adhesive layer formed on at least a part of the substrate layer and containing a hydrophilic copolymer (1) containing a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C) having a photoreactive group; and a surface lubricious layer formed on at least a part of the adhesive layer and containing a polymer containing a structural unit derived from acrylamide and a hydrophilic copolymer (2) containing a structural unit derived from a polymerizable monomer (A') having a sulfobetaine structure, a structural unit derived from a polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and a structural unit derived from a polymerizable monomer (C') having a photoreactive group.

[Substrate Layer (Substrate)]

The substrate layer used in this aspect may be constituted by any material as long as the material can react with the photoreactive group contained in the hydrophilic copolymer (1), which will be described later, to form a chemical bond. Specifically, examples of the material constituting (forming) the substrate layer 1 include a metal material, a polymer material, ceramics. Here, as shown in FIG. 1, the substrate layer 1 may be entirely (wholly) constituted (formed) by any one of the above materials, or, as shown in FIG. 2, the substrate layer 1 may have a configuration in which a surface of the substrate layer core portion 1*a* constituted (formed) by any one of the above materials is covered (coated) with any other of the above materials by an appropriate method to constitute (form) the substrate surface layer 1*b*. Examples of the latter case include a configuration in which a metal material is covered (coated) by an appropriate method (a known method in the related art such as plating, metal deposition, and sputtering) on the surface of the substrate layer core portion 1*a* formed by a resin material or the like to form the substrate surface layer 1*b*, and a configuration in which on the surface of the substrate layer core portion 1*a* formed by a hard reinforcing material such as a metal material or a ceramic material, a polymer material that is more flexible than the reinforcing material such as a metal material is covered (coated) by an appropriate method (a known method in the related art such as dipping, spraying, coating, and printing), or the reinforcing material of the substrate layer core portion 1*a* and the polymer material of the substrate surface layer 1*b* are composited (an appropriate reaction treatment), so as to form the substrate surface layer 1 b. Therefore, the substrate layer core portion 1*a* may be a multilayer structure in which different materials are laminated in multiple layers, a structure (composite) in which members made of different materials for each part of the medical device are connected to each other, or the like. Another middle layer (not shown) may be formed between the substrate layer core portion 1*a* and the substrate surface layer 1*b*. The substrate surface layer 1*b* may also be a multilayer structure in which different materials are laminated in multiple layers, a structure (composite) in which members made of different materials for each part of the medical device are connected to each other, or the like.

Among the materials constituting (forming) the above substrate layer 1, the metal material is not particularly limited, and metal materials commonly used in medical devices such as a catheter, a stent and a guide wire are used. Specific examples thereof include various stainless steels (SUS) such as SUS304, SUS316, SUS316L, SUS420J2, and SUS630, gold, platinum, silver, copper, nickel, cobalt, titanium, iron, aluminum, tin, and various alloys such as a nickel-titanium (Ni—Ti) alloy, a nickel-cobalt (Ni—Co) alloy, a cobalt-chromium (Co—Cr) alloy, and a zinc-tungsten (Zn—W) alloy. These metal materials may be used alone or in combination of two or more types thereof. The most suitable metal material as a substrate layer for a catheter, a stent, a guide wire, or the like, which is the intended use, may be appropriately selected for the above metal materials.

Among the materials constituting (forming) the above substrate layer 1, the polymer material is not particularly limited, and polymer materials commonly used in medical devices such as a catheter, a stent and a guide wire are used. Specific examples thereof include polyamide resins, polyethylenes such as a linear low density polyethylene (LLDPE), a low density polyethylene (LDPE), a high density polyethylene (HDPE), and a modified polyethylene, polyolefin resins such as polypropylene, polyester resins such as polyethylene terephthalate, polystyrene resins such as polystyrene, cyclic polyolefin resins, modified polyolefin resins, epoxy resins, urethane resins, diallyl phthalate resins (allyl resin), polycarbonate resins, fluororesin, amino resins (a urea resin, a melamine resin, and a benzoguanamine resin), acrylic resins, polyacetal resins, vinyl acetate resins, phenol resins, vinyl chloride resins, silicone resins (silicon resins), polyether resins such as polyetheretherketone (PEEK), and polyimide resins. From the viewpoint of adhesiveness to the adhesive layer described later, polyethylenes such as a high density polyethylene (HDPE) and a modified polyethylene, polyether resins such as polyetheretherketone (PEEK), and polyamide resins are preferred. These polymer materials may be used alone or in combination of two or more types thereof. The most suitable polymer material as a substrate layer for a catheter, a stent, a guide wire, or the like, which is the intended use, may be appropriately selected for the above polymer materials.

A shape of the above substrate layer is not particularly limited, and is appropriately selected as a sheet shape, a linear (wire) shape, a tubular shape, and the like depending on the form of the substrate layer to be used.

[Adhesive Layer (Hydrophilic Copolymer (1))]

The adhesive layer is formed on at least a part of the substrate layer and contains the hydrophilic copolymer (1) containing the structural unit derived from the polymerizable monomer (A) having a sulfobetaine structure (structural unit (A)), the structural unit derived from the polymerizable monomer (B) having at least one group selected from the group consisting of a sulfonic acid group (—$SO_3H$), a sulfuric acid group (—$OSO_3H$), a sulfurous acid group (—$OSO_2H$), and salt groups thereof (structural unit (B)), and the structural unit derived from the polymerizable monomer (C) having a photoreactive group (structural unit (C)). Here, the adhesive layer is not necessarily formed on the entire surface of the substrate layer. For example, the adhesive layer may be formed on a surface portion (a part) of the substrate layer to be in contact with the body fluid.

The hydrophilic copolymer (1) contained in the adhesive layer according to the disclosure contains the structural unit (the structural unit (A)) derived from the polymerizable monomer (A) (hereinafter, also referred to as a "monomer A") having a sulfobetaine structure, the structural unit (the structural unit (B)) derived from the polymerizable monomer (B) (hereinafter, also referred to as a "monomer B") having at least one group selected from the group consisting of a sulfonic acid group (—$SO_3H$), a sulfuric acid group (—$OSO_3H$), a sulfurous acid group (—$OSO_2H$), and salt groups thereof, and the structural unit (the structural unit (C)) derived from the polymerizable monomer (C) (hereinafter, also referred to as a "monomer C") having a photoreactive group. The hydrophilic copolymer (1) (hence, the adhesive layer) can exhibit a sufficient lubricating property and sufficient durability (lubrication retaining property). The hydrophilic copolymer (1) has good bondability (adhesiveness) to the substrate layer and the hydrophilic copolymer (2) or the polymer containing a structural unit derived from acrylamide as the water-retaining material in the surface lubricious layer described later. A mechanism by which such an effect is produced is not completely unclear, but the following mechanism is theorized. The photoreactive group contained in the structural unit derived from the monomer C generates reactive species by the irradiation with the active energy rays, and reacts with the surface of the substrate layer and the hydrophilic copolymer (2) or the polymer containing a structural unit derived from acrylamide in the surface lubricious layer described later to form a chemical bond. Therefore, the adhesive layer containing the hydrophilic copolymer (1) according to the disclosure is firmly immobilized on the substrate layer, and firmly immobilizes the surface lubricious layer, so that the durability (lubrication retaining property) is excellent. Note that the above mechanism is theory, and the invention is not limited to the above theory.

In the medical device, another layer may be provided between the adhesive layer and the substrate layer as long as another layer does not influence functions and effects of the medical device, and preferably, the adhesive layer is directly disposed above the substrate layer.

A thickness of the adhesive layer is not particularly limited. From the viewpoints of the adhesiveness to the substrate layer, the adhesiveness to the surface lubricious layer, the lubricating property, and the like, the thickness (dry film thickness) of the adhesive layer is preferably 0.1 μm to 100 μm, and more preferably 0.2 μm to 50 μm.

Hereinafter, each polymerizable monomer constituting the hydrophilic copolymer (1) contained in the adhesive layer according to the disclosure will be described.

(Polymerizable Monomer (A))

The hydrophilic copolymer (1) contains the structural unit derived from the polymerizable monomer (A) having a sulfobetaine structure (structural unit (A)). Here, the structural unit (A) constituting the hydrophilic copolymer (1) may be one type alone or a combination of two or more types. That is, the structural unit (A) may be constituted by only one type of structural unit (A), or may be constituted by two or more types of structural units (A). Note that a plurality of structural units (A) may be present in a block shape or in a random shape.

The polymerizable monomer (A) (monomer A) is a polymerizable monomer having a sulfobetaine structure. The sulfobetaine structure included in the structural unit derived from the monomer A is excellent in effect of imparting the lubricating property. Therefore, the hydrophilic copolymer (1) containing the structural unit derived from the monomer A is considered to be excellent in lubricating property. A homopolymer of the monomer A is soluble in an aqueous NaCl solution, but is insoluble or difficult to dissolve in water or a lower alcohol. Therefore, it is suggested that the sulfobetaine structure may have a strong electrostatic interaction. Therefore, a strong cohesive force acts inside the adhesive layer containing the hydrophilic copolymer (1) according to the disclosure. Accordingly, the adhesive layer is considered to have high strength (excellent in durability). Note that the above is theory, and the invention is not limited to the above theory.

Here, the "sulfobetaine structure" refers to a structure in which a positive charge and a negative charge containing a sulfur element are present in positions not adjacent to each other, a dissociable hydrogen atom is not bonded to an atom having the positive charge, and a sum of the charges is zero.

The monomer A is not particularly limited, and examples thereof include compounds represented by the following general formulas.

[Chem. 1]

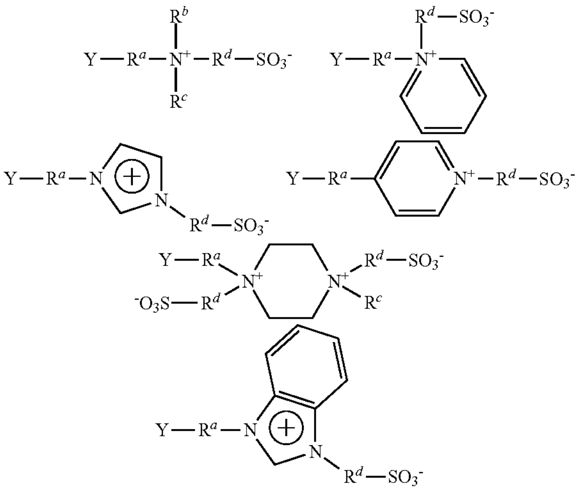

In the above general formulas, $R^a$ and $R^d$ may each independently represent a substitutable alkylene group having 1 to 30 carbon atoms or a substitutable arylene group having 6 to 30 carbon atoms. $R^b$ and $R^c$ may each independently represent a substitutable alkyl group having 1 to 30 carbon atoms or a substitutable aryl group having 6 to 30 carbon atoms. Y may represent a group having an ethylenically unsaturated group such as an acryloyl group ($CH_2$=CH—C(=O)—), a methacryloyl group ($CH_2$=C($CH_3$)—C(=O)—), and a vinyl group ($CH_2$=CH—). Here, in the above general formulas, the sum of the positive charges and the negative charges is zero.

Examples of the alkylene group having 1 to 30 carbon atoms include a methylene group, an ethylene group, a trimethylene group, a propylene group, an isopropylene group, a butylene group, an isobutylene group, a sec-butylene group, a tert-butylene group, and a pentylene group.

Examples of the arylene group having 6 to 30 carbon atoms include a phenylene group, a naphthylene group, an anthracenylene group, a phenanthrenylene group, a pyrenylene group, a peryleneylene group, a fluorenylene group, and a biphenylene group.

Examples of the alkyl group having 1 to 30 carbon atoms include a methyl group, an ethyl group, a n-propyl group, an isopropyl group, a n-butyl group, an isobutyl group, a sec-butyl group, a tert-butyl group, a n-pentyl group, an iso-amyl group, a tert-pentyl group, a neopentyl group, and a n-hexyl group.

Examples of the aryl group having 6 to 30 carbon atoms include a phenyl group, a biphenyl group, a terphenyl group, a pentarenyl group, an indenyl group, a naphthyl group, an azulenyl group, a heptalenyl group, and a biphenylenyl group.

Among these, from the viewpoint of further improving the lubricating property and the durability (lubrication retaining property), the monomer A is preferably a compound represented by the following formula (1). That is, in a preferred embodiment of the medical device, the polymerizable monomer (A) is a compound represented by the following formula (1).

[Chem. 2]

(1)

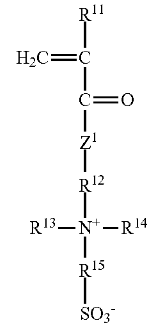

In the above formula (1), $R^{11}$ represents a hydrogen atom or a methyl group. $Z^1$ represents an oxygen atom (—O—) or —NH—, and preferably an oxygen atom (—O—).

In the above formula (1), from the viewpoint of further improving the lubricating property and the durability (lubrication retaining property), $R^{12}$ and $R^{15}$ each independently represent a linear or branched alkylene group having 1 to 20 carbon atoms, preferably a linear or branched alkylene group having 1 to 12 carbon atoms, more preferably a linear or branched alkylene group having 1 to 8 carbon atoms, still more preferably a linear or branched alkylene group having 1 to 6 carbon atoms, even more preferably a linear alkylene group having 1 to 4 carbon atoms (methylene group, ethylene group, trimethylene group, or tetramethylene group), and particularly preferably a linear alkylene group having 1 to 3 carbon atoms (methylene group, ethylene group, or trimethylene group). From the viewpoint of further improving the lubricating property and the durability (lubrication retaining property), as a combination of $R^{12}$ and $R^{15}$, $R^{12}$ preferably represents an ethylene group and $R^{15}$ preferably represents a trimethylene group, or $R^{12}$ preferably represents a trimethylene group and $R^{15}$ preferably represents a tetramethylene group.

In the above formula (1), from the viewpoint of further improving the lubricating property and the durability (lubrication retaining property), $R^{13}$ and $R^{14}$ each independently represent a linear or branched alkyl group having 1 to 20 carbon atoms, preferably a linear or branched alkyl group having 1 to 12 carbon atoms, more preferably a linear or branched alkyl group having 1 to 8 carbon atoms, still more preferably a linear or branched alkyl group having 1 to 4 carbon atoms, and particularly preferably a methyl group.

Examples of the compound represented by the above formula (1) include {2-[(meth)acryloyloxy]ethyl}dimethyl-(3-sulfopropyl)ammonium hydroxide, {2-[(meth)acryloyloxy]ethyl}dimethyl-(2-sulfoethyl)ammonium hydroxide, {2-[(meth)acryloyloxy]ethyl}dimethyl-(2-sulfobutyl)ammonium hydroxide, {2-[(meth)acryloyloxy]ethyl}diethyl-(2-sulfoethyl)ammonium hydroxide, {2-[(meth)acryloyloxy]ethyl}diethyl-(3-sulfopropyl)ammonium hydroxide, {2-[(meth)acryloyloxy]ethyl}diethyl-(2-sulfobutyl)ammonium hydroxide, {3-[(meth)acryloyloxy]propyl}dimethyl-(2-sulfoethyl)ammonium hydroxide, {3-[(meth)acryloyloxy]propyl}dimethyl-(3-sulfopropyl)ammonium hydroxide, {3-[(meth)acryloylamino)propyl}dimethyl(3-sulfobutyl)ammonium hydroxide, {3-[(meth)acryloyloxy]propyl}diethyl-(2-sulfoethyl)ammonium hydroxide, {3-[(meth)acryloyloxy]propyl}diethyl-(3-sulfopropyl) ammonium hydroxide, and {3-[(meth)acryloyloxy]propyl}diethyl-(3-sulfobutyl)ammonium hydroxide. Among these, {2-[(meth)acryloyloxy]ethyl}dimethyl-(3-sulfopropyl)ammonium hydroxide and {3-[(meth)acryloyloxy)propyl]dimethyl(3-sulfobutyl)ammonium hydroxide are preferred, {2-[methacryloyloxy]ethyl}dimethyl-(3-sulfopropyl)ammonium hydroxide (MSPB) and [3-(methacryloylamino)propyl]dimethyl(3-sulfobutyl) ammonium hydroxide (MSBB) are more preferred, and {2-[methacryloyloxy]ethyl}dimethyl-(3-sulfopropyl)ammonium hydroxide (MSPB) is still more preferred. The above compounds may be used alone or in combination of two or more types thereof.

As the monomer A, either a synthetic product or a commercially available product may be used. The commercially available product is available from Sigma-Aldrich Co. LLC., Fujifilm Wako Pure Chemical Cooperation, and the like. An exemplary compound may be synthesized with reference to A. Laschewsky, polymers, 6, 1544-1601 (2014), and the like.

The monomer A is not limited to the compounds represented by the above general formulas, and may be a compound having a form in which a positive charge is present at a terminal end.

In the hydrophilic copolymer (1), when a total of structural units derived from all the monomers is 100 mol %, a content of the structural unit derived from the monomer A is preferably 0.1 mol % to 99 mol %, more preferably 1 mol % to 99 mol %, still more preferably 5 mol % to 99 mol %, and particularly preferably 10 mol % to 99 mol %. Within such a range, a balance between the lubricating property and the solvent solubility is good. Note that when the structural unit (A) is constituted by two or more types of structural units (A), a composition of the above structural unit (A) occupies a ratio (molar ratio (mol %)) of all the structural units (A) with respect to the total of the structural units derived from all the monomers (100 mol %). The mol % is substantially equivalent to a ratio of a charge amount (mol) of the monomer A with respect to a total charge amount (mol) of all the monomers in the production of the polymer.

(Polymerizable Monomer (B))

The hydrophilic copolymer (1) contains the structural unit derived from the polymerizable monomer (B) having at least one group selected from the group consisting of a sulfonic acid group ($—SO_3H$), a sulfuric acid group ($—OSO_3H$), a sulfurous acid group ($—OSO_2H$), and salt groups thereof (structural unit (B)). Here, the structural unit (B) constituting the hydrophilic copolymer (1) may be one type alone or a combination of two or more types. That is, the structural unit (B) may be constituted by only one type of structural unit (B), or may be constituted by two or more types of structural units (B). Note that a plurality of structural units (B) may be present in a block shape or in a random shape.

The polymerizable monomer (B) (monomer B) is a polymerizable monomer having at least one group selected from the group consisting of a sulfonic acid group ($—SO_3H$), a sulfuric acid group ($—OSO_3H$), a sulfurous acid group ($—OSO_2H$), and salt groups thereof. By introducing such a group, anionization occurs in an aqueous solvent, and electrostatic repulsion occurs between the hydrophilic copolymers. As a result, an electrostatic interaction between the sulfobetaine structures and a hydrophobic interaction between the photoreactive groups in the hydrophilic copolymers are reduced. Therefore, the solvent solubility of the copolymer (particularly the solubility in water, a lower alcohol, or a mixed solvent of water and a lower alcohol) is improved. This improving effect is particularly remarkable when the photoreactive group of the monomer C is a benzophenone group. Since the benzophenone group has a plurality of aromatic rings, the benzophenone groups are likely to associate with each other by a π-π interaction, which makes the polymers containing the benzophenone group to aggregate and insolubilize. Therefore, it is considered that by introducing the structural unit derived from the monomer B, the electrostatic repulsion occurs as described above, and the association between the benzophenone groups is reduced, and thus the solubility or dispersibility of the polymer is rapidly improved. Note that the above mechanism is theory, and the invention is not limited to the above theory. Alternatively, even when the monomer C has an ester group, the above improving effect can be obtained satisfactorily. In addition to the above groups, the monomer B preferably has an ethylenically unsaturated group such as a (meth)acryloyl group, a vinyl group, or an allyl group.

Among these, from the viewpoint of further improving the solvent solubility, the monomer (B) is preferably a compound represented by the following formula (2), (3), or (4), and more preferably a compound represented by the following formula (2). That is, in a preferred embodiment of the medical device, the polymerizable monomer (B) is a compound represented by the following formula (2), (3), or (4). In a more preferred embodiment of the medical device, the polymerizable monomer (B) is a compound represented by the following formula (2).

[Chem. 3]

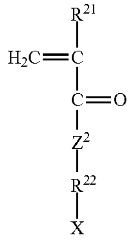

(2)

In the above formula (2), $R^{21}$ represents a hydrogen atom or a methyl group. $Z^2$ represents an oxygen atom (—O—) or —NH—, and preferably —NH—.

In the above formula (2), from the viewpoint of further improving the solvent solubility, $R^{22}$ represents a linear or branched alkylene group having 1 to 20 carbon atoms, preferably a linear or branched alkylene group having 1 to 12 carbon atoms, more preferably a linear or branched alkylene group having 1 to 8 carbon atoms, still more preferably a linear or branched alkylene group having 1 to 6 carbon atoms, and particularly preferably a branched alkylene group having 3 to 5 carbon atoms. The branched alkylene group having 3 to 5 carbon atoms is a group represented by $—CH(CH_3)—CH_2—$, $—C(CH_3)_2—CH_2—$, $—CH(CH_3)—CH(CH_3)—$, $—C(CH_3)_2—CH_2—CH_2—$, $—CH(CH_3)—CH(CH_3)—CH_2—$, $—CH(CH_3)—CH_2—CH(CH_3)—$, $—CH_2—C(CH_3)_2—CH_2—$, $—C(CH_3)_2—CH(CH_3)—$, or the like (a connection order of the above groups in the above formula (2) is not particularly limited), and among these, a group represented by $—C(CH_3)_2—CH_2—$ is particularly preferred.

In the above formula (2), X represents a group selected from the group consisting of a sulfonic acid group ($—SO_3H$), a sulfuric acid group ($—OSO_3H$), a sulfurous acid group ($—OSO_2H$), and salt groups thereof. From the viewpoints of acid dissociation (that is, ease of anionization) and even the solvent solubility of the copolymer, X preferably represents a group selected from the group consisting of a sulfonic acid group, a sulfuric acid group, and salt groups thereof. From the viewpoint of easy availability of monomers, X more preferably represents a sulfonic acid group or a salt group thereof. Here, the salt is not particularly limited, and for example, the salt may be an alkali metal salt (sodium salt, potassium salt, or the like) of the above group.

Examples of the compound represented by the above formula (2) include 2-(meth)acrylamide-2-methyl-1-propanesulfonic acid, 1-[(meth)acryloyloxymethyl]-1-propanesulfonic acid, 2-[(meth)acryloyloxy]-2-propanesulfonic acid, 3-[(meth)acryloyloxy]-1-methyl-1-propanesulfonic acid, 2-sulfoethyl (meth)acrylate, 3-sulfopropyl (meth)acrylate, and salts thereof (preferably a sodium salt or a potassium salt). Among these, 2-(meth)acrylamide-2-methyl-1-propanesulfonic acid or a salt thereof (particularly alkali metal salt) is preferred, and 2-acrylamide-2-methyl-1-propanesulfonic acid or a salt thereof (particularly sodium salt) is more preferred. These compounds may be used alone or in combination of two or more types thereof.

The compound represented by the above formula (2) may be either a synthetic product or a commercially available product, and the commercially available product is available from Tokyo Chemical Industry Co., Ltd., Sigma-Aldrich Co. LLC., and the like.

[Chem. 4]

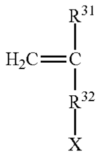

(3)

In the above formula (3), $R^{31}$ represents a hydrogen atom or a methyl group.

In the above formula (3), $R^{32}$ represents a single bond or a linear or branched alkylene group having 1 to 20 carbon atoms, preferably a single bond or a linear or branched alkylene group having 1 to 12 carbon atoms, more preferably a single bond or a linear or branched alkylene group having 1 to 8 carbon atoms, still more preferably a single bond or a linear or branched alkylene group having 1 to 4 carbon atoms, and particularly preferably a single bond. Here, since specific examples of the alkylene group are the same as those for the above formula (2), description thereof will be omitted here.

In the above formula (3), X represents a group selected from the group consisting of a sulfonic acid group ($—SO_3H$), a sulfuric acid group ($—OSO_3H$), a sulfurous acid group ($—OSO_2H$), and salt groups thereof. From the viewpoints of the acid dissociation (that is, the ease of anionization) and even the solvent solubility of the copolymer, X preferably represents a group selected from the group consisting of a sulfonic acid group, a sulfuric acid group, and salt groups thereof. From the viewpoint of easy availability of monomers, X more preferably represents a sulfonic acid group or a salt group thereof.

Examples of the compound represented by the above formula (3) include vinyl sulfonic acid, allyl sulfonic acid, methallyl sulfonic acid, 2-propene-1-sulfonic acid, 2-methyl-2-propene-1-sulfonic acid, and salts thereof. These compounds may be used alone or in combination of two or more types thereof.

The compound represented by the above formula (3) may be either a synthetic product or a commercially available product, and the commercially available product is available from Asahi Kasei Finechem Co., Ltd., Tokyo Chemical Industry Co., Ltd. (for example, sodium salt of 2-methyl-2-propene-1-sulfonic acid), and the like.

[Chem. 5]

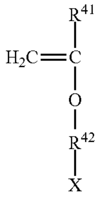

(4)

In the above formula (4), $R^{41}$ represents a hydrogen atom or a methyl group.

In the above formula (4), $R^{42}$ represents a linear or branched alkylene group having 1 to 20 carbon atoms, preferably a linear or branched alkylene group having 1 to 12 carbon atoms, more preferably a linear or branched alkylene group having 1 to 8 carbon atoms, and still more preferably a linear or branched alkylene group having 1 to 6 carbon atoms. Here, since specific examples of the alkylene group are the same as those for the above formula (2), description thereof will be omitted here.

In the above formula (4), X represents a group selected from the group consisting of a sulfonic acid group ($—SO_3H$), a sulfuric acid group ($—OSO_3H$), a sulfurous acid group ($—OSO_2H$), and salt groups thereof. From the viewpoints of the acid dissociation (that is, the ease of anionization) and even the solvent solubility of the copolymer, X preferably represents a group selected from the group consisting of a sulfonic acid group, a sulfuric acid group, and salt groups thereof. From the viewpoint of easy availability of monomers, X more preferably represents a sulfonic acid group or a salt group thereof.

Examples of the compound represented by the above formula (4) include 2-sulfoxyethyl vinyl ether, 3-sulfoxy-n-propyl vinyl ether, and salts thereof. These compounds may be used alone or in combination of two or more types thereof.

As the compound represented by the above formula (4), either a synthetic product or a commercially available product may be used.

In the hydrophilic copolymer (1), when the total of the structural units derived from all the monomers is 100 mol %, a content of the structural unit derived from the monomer B is preferably 0.1 mol % to 99 mol %, more preferably 0.2 mol % to 99 mol %, still more preferably 0.5 mol % to 99 mol %, and particularly preferably 1 mol % to 99 mol %. Within such a range, the balance between the lubricating property and the solvent solubility is good. Note that when the structural unit (B) is constituted by two or more types of structural units (B), a composition of the above structural unit (B) occupies a ratio (molar ratio (mol %)) of all the structural units (B) with respect to the total of the structural units derived from all the monomers (100 mol %). The mol % is substantially equivalent to a ratio of a charge amount (mol) of the monomer B with respect to the total charge amount (mol) of all the monomers in the production of the polymer.

(Polymerizable Monomer (C))

The hydrophilic copolymer (1) contains the structural unit derived from the polymerizable monomer (C) having a photoreactive group (structural unit (C)). Here, the structural unit (C) constituting the hydrophilic copolymer (1) may be one type alone or a combination of two or more types. That is, the structural unit (C) may be constituted by only one type of structural unit (C), or may be constituted by two or more types of structural units (C). Note that a plurality of structural units (C) may be present in a block shape or in a random shape.

The polymerizable monomer (C) (monomer C) is a polymerizable monomer having a photoreactive group. Here, the "photoreactive group" refers to a group that can generate reactive species such as radicals, nitrenes, and carbenes by being irradiated with active energy rays and react with the substrate layer (resin) and the surface lubricious layer (the hydrophilic copolymer (2) and the polymer containing a structural unit derived from acrylamide) to form a chemical bond. Accordingly, the adhesive layer containing the hydrophilic copolymer (1) can firmly immobilize the substrate layer and the surface of the surface lubricious layer. Therefore, by disposing the adhesive layer between the substrate layer and the surface lubricious layer, the medical device can exhibit sufficient durability (lubrication retaining property). The monomer C preferably has an ethylenically unsaturated group such as a (meth)acryloyl group, a vinyl group, or an allyl group, in addition to the above photoreactive group.

Examples of the photoreactive group include an azide group, a diazo group, a diazirine group, a ketone group, and a quinone group.

Examples of the azide group include an aryl azide group of phenyl azide and 4-fluoro-3-nitrophenyl azide, an acyl azide group of benzoyl azide and p-methylbenzoyl azide, an azidoformate group of ethyl azideformate and phenyl azideformate, a sulfonyl azide group of benzenesulfonyl azide, and a phosphoryl azide group of diphenylphosphoryl azide and diethyl phosphoryl azide.

Examples of the diazo group include a group derived from diazoalkanes such as diazomethane and diphenyldiazomethane, diazoketones such as diazoacetophenone and 1-trifluoromethyl-1-diazo-2-pentanone, diazoacetates such as t-butyldiazoacetate and phenyldiazoacetate, and α-diazoacetoacetates such as t-butyl-α-diazoacetoacetate.

Examples of the diazirine group include a group derived from 3-trifluoromethyl-3-phenyldiazirine.

Examples of the ketone group include a group having a structure such as acetophenone, benzophenone, anthrone, xanthine, and thioxanthone.

Examples of the quinone group include a group derived from anthraquinone.

These photoreactive groups are appropriately selected depending on the type of the substrate layer of the medical device and the like. For example, when the substrate layer is made of a polyolefin resin such as a polyethylene resin, a polyamide resin, a polyurethane resin, a polyester resin, or the like, the photoreactive group is preferably a ketone group or a phenyl azide group, and more preferably a group having a benzophenone structure (a benzophenone group) from the viewpoint of easy availability of monomers. That is, in a preferred embodiment of the medical device, the polymerizable monomer (C) has a group having a benzophenone structure.

Examples of the monomer C include 2-azidoethyl(meth) acrylate, 2-azidopropyl(meth)acrylate, 3-azidopropyl(meth) acrylate, 4-azidobutyl(meth)acrylate, 4-(meth)acryloyloxybenzophenone (MBP), 4-(meth)acryloyloxyethoxybenzophenone, 4-(meth)acryloyloxy-4'-methoxybenzophenone, 4-(m eth)acryloyloxyethoxy-4'-methoxybenzophenone, 4-(meth)acryloyloxy-4'-bromobenzophenone, 4-(meth)acryloyloxyethoxy-4'-bromobenzophenone, 4-styrylmethoxybenzophenone, 4-(meth)acryloyloxythioxanthone, and 2-(meth)achryloyloxyethyl-4-azidobenzoate.

As the monomer C, either a synthetic product or a commercially available product may be used, and the commercially available product is available from MCC UNITEC Co., Ltd. or the like.

In the hydrophilic copolymer (1), when the total of the structural units derived from all the monomers is 100 mol %, a content of the structural unit derived from the monomer C is preferably 0.1 mol % to 40 mol %, more preferably 0.1 mol % to 30 mol %, still more preferably 0.1 mol % to 25 mol %, and particularly preferably 0.1 mol % to 20 mol %. Within such a range, the hydrophilic copolymer (1) can be sufficiently bonded to the substrate layer (resin) and the surface lubricious layer (the hydrophilic copolymer (2) and the polymer containing a structural unit derived from acrylamide). Accordingly, the adhesive layer containing the hydrophilic copolymer (1) can immobilize the substrate layer and the surface lubricious layer more firmly. Within such a range, a sufficient amount of other monomers (the monomers A and B) can be present, so that the sufficient lubricating property and the durability by the monomer A and the solvent solubility by the monomer B in the hydrophilic copolymer (1) can be more effectively improved. Note that when the structural unit (C) is constituted by two or more types of structural units (C), a composition of the above structural unit (C) occupies a ratio (molar ratio (mol %)) of all the structural units (C) with respect to the total of the structural units derived from all the monomers (100 mol %). The mol % is substantially equivalent to a ratio of a charge amount (mol) of the monomer C with respect to the total charge amount (mol) of all the monomers in the production of the polymer.

The hydrophilic copolymer (1) may contain a structural unit derived from a polymerizable monomer other than the above monomer A, monomer B, and monomer C (hereinafter, also referred to as "other monomer") in a range that does not impair the effects of the medical device. In the hydrophilic copolymer (1) according to the disclosure, a content of the structural unit derived from the other monomer is preferably less than 10 mol %, more preferably less than 5 mol %, and still more preferably less than 1 mol % (lower limit: more than 0 mol %), with respect to 100 mol %, which is the total of the structural units derived from all the monomers. Note that when the structural unit derived from the other monomer is constituted by two or more types of structural units, a composition of the above structural unit derived from the other monomer occupies a ratio (molar ratio (mol %)) of all the structural units derived from the other monomer with respect to the total of the structural units derived from all the monomers (100 mol %). Preferably, the hydrophilic copolymer (1) according to the disclosure is constituted only by the monomer A, the monomer B, and the monomer C (the composition of the other monomer=0 mol %). Note that the mol % is substantially equivalent to a ratio of a charge amount (mol) of the other monomer with respect to the total charge amount (mol) of all the monomers in the production of the polymer.

A terminal end of the hydrophilic copolymer (1) is not particularly limited and is appropriately defined depending on types of raw materials to be used, and is usually a hydrogen atom. A structure of the copolymer is not particularly limited, and may be any of a random copolymer, an alternating copolymer, a periodic copolymer, and a block copolymer.

A weight average molecular weight (Mw) of the hydrophilic copolymer (1) is preferably several thousand to several million, more preferably 1,000 to 1,000,000, and particularly preferably 5,000 to 500,000. In the disclosure, the "weight average molecular weight" shall be a value measured by gel permeation chromatography (GPC) using polyethylene glycol as a standard substance.

[Method for Manufacturing Hydrophilic Copolymer (1)]

A method for manufacturing the hydrophilic copolymer (1) is not particularly limited, and known polymerization methods such as radical polymerization, anionic polymerization, and cationic polymerization can be adopted. The radical polymerization that is easy in production is preferably used.

As the polymerization method, a method of copolymerizing the above monomer A, monomer B, monomer C, and if necessary, the other monomer by stirring and heating together with a polymerization initiator in a polymerization solvent is usually adopted.

A polymerization temperature is not particularly limited, and is preferably 25° C. to 100° C., and more preferably 30°

C. to 80° C. A polymerization time is also not particularly limited, and is preferably 30 minutes to 24 hours, and more preferably 1 hour to 8 hours.

The polymerization solvent is preferably water, and an aqueous solvent such as alcohols such as methanol, ethanol, propanol, n-butanol, and 2,2,2-trifluoroethanol. From the viewpoint of dissolving raw materials to be used for the polymerization, these polymerization solvents may be used alone or in combination of two or more types thereof.

A concentration of the polymerizable monomers is not particularly limited, and a total solid content (g) of each polymerizable monomer with respect to the polymerization solvent (mL) is preferably 0.05 g/mL to 1 g/mL, and more preferably 0.1 g/mL to 0.5 g/mL. The preferred ratio of the charge amount (mol) of each monomer to the total charge amount (mol) of all the monomers is as described above.

A reaction solution containing the polymerizable monomers may be subjected to a degassing treatment before the polymerization initiator is added. The degassing treatment may be performed by, for example, bubbling the reaction solution with an inert gas such as nitrogen gas and argon gas for approximately 0.5 hours to 5 hours. During the degassing treatment, the reaction solution may be heated to approximately 30° C. to 100° C.

Known polymerization initiators in the related art can be used in the production of the polymer, and the polymerization initiator is not particularly limited. For example, an azo-based polymerization initiator such as 2,2'-azobisisobutyronitrile, 2,2'-azobis(4-methoxy-2,4-dimethylvaleronitrile), 4,4'-azobis(4-cyanovaleric acid), and 2,2'-azobis(2,4-dimethylvaleronitrile), and a redox-based polymerization initiator in which a reducing agent such as sodium sulfite, sodium hydrogen sulfite, and ascorbic acid is combined with an oxidizing agent such as a persulfate such as potassium persulfate (KPS), sodium persulfate, and ammonium persulfate, and a peroxide such as hydrogen peroxide, t-butyl peroxide, and methyl ethyl ketone peroxide can be used.

A blending amount of the polymerization initiator is preferably 0.001 mol % to 10 mol %, and more preferably 0.01 mol % to 5 mol % with respect to a total amount (mol) of the polymerizable monomers.

Further, if necessary, a chain transfer agent, a polymerization rate adjusting agent, a surfactant, and other additives may be appropriately used in the polymerization.

An atmosphere in which the polymerization reaction is performed is not particularly limited, and the polymerization reaction can be performed in air atmosphere, an atmosphere of an inert gas such as nitrogen gas and argon gas, and the like. During the polymerization reaction, the reaction solution may be stirred.

The copolymer may be precipitated during the polymerization reaction. The copolymer after polymerization can be purified by a general purification method such as a reprecipitation method, a dialysis method, an ultrafiltration method, and an extraction method.

The copolymer after purification can be dried by any method such as freeze drying, vacuum drying, spray drying, and heat drying, and from the viewpoint of having a small influence on physical properties of the polymer, freeze drying or vacuum drying is preferred.

Unreacted monomers contained in the obtained copolymer are preferably 0.01 wt % or less with respect to the total amount of the copolymer. A smaller amount of unreacted monomers is preferred (lower limit: 0 wt %). A content of the remaining monomers can be measured by a known method such as high performance liquid chromatography.

The presence and the ratio of the structural unit derived from each polymerizable monomer in the hydrophilic copolymer (1) in the adhesive layer can be confirmed by, for example, analyzing peak intensity of a group contained in each structural unit using a known method such as IR, NMR, and pyrolysis GC/MS. In the present description, the presence and the ratio of the structural unit derived from each polymerizable monomer in the hydrophilic copolymer (1) in the adhesive layer are measured according to the following method.

(Method for Detecting and Measuring Presence and Ratio of Structural Unit Derived from Each Polymerizable Monomer in Hydrophilic Copolymer (1) in Adhesive Layer)

With the surface of the medical device swollen with heavy water or the like, precision diagonal cutting is performed on the medical device to prepare an inclined cross section of the medical device. From the cross section, an adhesive layer portion located near the substrate of the medical device is cut, and a material of the adhesive layer portion is collected. Next, the material of the adhesive layer portion is filled into a sample tube for solid NMR without any gap to prepare a sample, and NMR measurement is performed. Here, peaks specific to a site (for example, a sulfobetaine structure) specific to the structural unit (A), a site (for example, a salt of a sulfonic acid group) specific to the structural unit (B), and a site (for example, a benzophenone group) specific to the structural unit (C) are to be confirmed, and when these peaks are confirmed, it is determined that the corresponding structural units are present in the sample. A concentration of the site (for example, the sulfobetaine structure) specific to the structural unit (A) (concentration (a)), a concentration of the site (for example, the salt of the sulfonic acid group) specific to the structural unit (B) (concentration (b)), and a concentration of the site (for example, the benzophenone group) specific to the structural unit (C) (concentration (c)) are measured. A ratio of each of the concentrations (a), (b), and (c) is regarded as an abundance ratio of the structural unit derived from each polymerizable monomer in the hydrophilic copolymer (1). Note that an analyzer and measurement conditions used in the above measurement are as follows.

Analyzer: NM080006, manufactured by JEOL Ltd. Measurement conditions: heavy water or a mixed liquid of heavy water and a heavy solvent of a lower alcohol.

[Surface Lubricious Layer]

The surface lubricious layer in the medical device is formed on at least a part of the adhesive layer and contains (i) the polymer containing a structural unit derived from acrylamide, and (ii) the hydrophilic copolymer (2) containing the structural unit derived from the polymerizable monomer (A') having a sulfobetaine structure, the structural unit derived from the polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof, and the structural unit derived from the polymerizable monomer (C') having a photoreactive group. Here, the surface lubricious layer is not necessarily formed on the entire surface of the adhesive layer. The surface lubricious layer may be formed on a surface portion (a part) of the adhesive layer to be in contact with a body fluid, and is preferably formed on the entire surface of the adhesive layer.

The surface lubricious layer contains (i) the polymer containing a structural unit derived from acrylamide (acrylamide-based polymer) and (ii) the hydrophilic copolymer (2). Of these, (ii) the hydrophilic copolymer (2) exhibits a lubricating property when wet (for example, when in contact with an aqueous liquid such as a body fluid or physiological saline). (i) The acrylamide-based polymer acts to retain the aqueous liquid. The presence of the acrylamide-based polymer moderately reduces the crosslink density of the surface lubricious layer. Therefore, the aqueous liquid easily enters the surface lubricious layer, and the hydrophilic copolymer (2) easily exhibits a lubricating property (gel hydration lubrication). In addition, under a high load condition, the surface lubricious layer forms a hydrated layer between the inner surface of the lumen in the living body and the medical device due to the aqueous liquid retained on the surface lubricious layer. Therefore, it is considered that the hydrophilic copolymer (2) can exhibit a lubricating property by being in contact with a sufficient amount of the aqueous liquid even under a high load condition. Note that the above mechanism is theory, and the invention is not limited to the above theory.

In the medical device, another layer may be provided between the surface lubricious layer and the adhesive layer as long as another layer does not influence functions and effects of the medical device, and preferably, the surface lubricious layer is directly disposed above the adhesive layer. In addition, another layer may be provided on the surface lubricious layer as long as the functions and effects of the medical device are not influenced, and it is preferable that another layer is not disposed on the surface lubricious layer (the surface lubricious layer is an outermost layer). According to this embodiment, the effect (lubricating property) of the medical device can be effectively exhibited.

A thickness of the surface lubricious layer is not particularly limited. From the viewpoints of the lubricating property, the durability (lubrication retaining property), the adhesiveness to the adhesive layer, and the like, the thickness (dry film thickness) of the surface lubricious layer is preferably 0.1 μm to 100 μm, and more preferably 0.2 μm to 50 μm.

Hereinafter, compositions (the polymer containing a structural unit derived from acrylamide and the hydrophilic copolymer (2)) contained in the surface lubricious layer according to the disclosure will be described.

(Polymer Containing Structural Unit Derived from Acrylamide)

The surface lubricious layer contains the polymer containing a structural unit derived from acrylamide (acrylamide structural unit), i.e., the following formula (acrylamide-based polymer).

[Chem. 6]

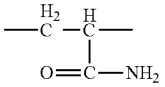

(Acrylamide structural unit)

The polymer containing a structural unit derived from acrylamide may contain a structural unit derived from another monomer, in addition to the above acrylamide structural unit. Here, another monomer that may be contained when the acrylamide-based polymer contains the structural unit derived from another monomer is not particularly limited as long as another monomer does not inhibit the water retention effect. Specific examples thereof include N,N-dimethylacrylamide, N-isopropylacrylamide, vinylpyrrolidone, acrylic acid, and acrylates (for example, sodium salt and potassium salt). Here, the structural unit derived from the above another monomer may be one type alone or a combination of two or more types. That is, the structural unit derived from another monomer may be constituted by only one type of structural unit, or may be constituted by two or more types of structural units. Note that a plurality of structural units derived from another monomer may be present in a block shape or in a random shape. In this embodiment, a content of the structural unit derived from another monomer is preferably less than 10 mol %, more preferably less than 5 mol %, and still more preferably less than 1 mol % (lower limit: 0 mol %), with respect to 100 mol %, which is the total of the structural units derived from all the monomers. Note that the mol % is substantially equivalent to a ratio of a charge amount (mol) of another monomer with respect to the total charge amount (mol) of all the monomers in the production of the polymer. Preferably, the polymer containing a structural unit derived from acrylamide according to the disclosure (acrylamide-based polymer) is preferably constituted by only acrylamide. That is, in a preferred embodiment of the medical device, the polymer containing a structural unit derived from acrylamide is polyacrylamide.

A molecular weight of the polymer containing a structural unit derived from acrylamide is not particularly limited. For example, a number average molecular weight (Mn) of the polymer containing a structural unit derived from acrylamide is 500 to 50,000,000, preferably 1,000 to 25,000,000, more preferably 1,000 to 20,000,000, still more preferably 5,000 to 10,000,000, particularly preferably 10,000 to 5,000,000, and most preferably 10,000 to 2,000,000. The acrylamide-based polymer in such a range can exhibit a sufficient water retention effect. In the disclosure, the "number average molecular weight" shall be a value measured by gel permeation chromatography (GPC) using polyethylene glycol as a standard substance.

As the polymer containing a structural unit derived from acrylamide, either a synthetic product or a commercially available product may be used. The commercially available product is available from Sigma-Aldrich Co. LLC. and the like.

(Hydrophilic Copolymer (2))

The surface lubricious layer contains the hydrophilic copolymer (2) in addition to the polymer containing a structural unit derived from acrylamide. The hydrophilic copolymer (2) contains the structural unit derived from the polymerizable monomer (A') having a sulfobetaine structure, the structural unit derived from the polymerizable monomer (B') having at least one group selected from the group consisting of a sulfonic acid group ($-SO_3H$), a sulfuric acid group ($-OSO_3H$), a sulfurous acid group ($-OSO_2H$), and salt groups thereof, and the structural unit derived from the polymerizable monomer (C') having a photoreactive group. The hydrophilic copolymer (2) contained in the surface lubricious layer may have a structure same as or different from that of the hydrophilic copolymer (1) contained in the adhesive layer. From the viewpoint of immobilization strength (hence durability) between the adhesive layer and the surface lubricious layer, the hydrophilic copolymer (1) and the hydrophilic copolymer (2) preferably have the same structure. In the above embodiment, only one process is required to manufacture the hydrophilic copolymer, and a use amount of the hydrophilic copolymer increases, which is therefore particularly preferable from the viewpoints of the number of production steps during mass production and a cost of products. Here, "the hydrophilic copolymer (1) and the hydrophilic copolymer (2) have the same structure" means that types of the structural units (A), (B), (C), and, if present, a structural unit derived from another monomer constituting the hydrophilic copolymer (1) are all the same as those of the structural units (A'), (B'), (C'), and, if present, a structural unit derived from another monomer constituting the hydrophilic copolymer (2), respectively (the hydrophilic copolymers (1) and (2) are constituted by the same structural units). From the viewpoints of further improving the immobilization strength (hence durability) between the adhesive layer and the surface lubricious layer, productivity, and the like, it is preferable that the types and compositions (content ratio (molar ratio)) of the structural units constituting the hydrophilic copolymers (1) and (2) are all the same (the hydrophilic copolymers (1) and (2) are constituted by the same structural units and the same compositions).

In the surface lubricious layer, an abundance ratio (mixing ratio) of the hydrophilic copolymer (2) with respect to the polymer containing a structural unit derived from acrylamide is not particularly limited. In the surface lubricious layer, for the abundance ratio (mixing ratio) of the hydrophilic copolymer (2) with respect to the polymer containing a structural unit derived from acrylamide, the hydrophilic copolymer (2) is preferably 0.5 parts by weight or more and less than 500 parts by weight, more preferably 0.5 parts by weight to 450 parts by weight, still more preferably 0.5 parts by weight to 350 parts by weight, even more preferably 0.5 parts by weight to 200 parts by weight, yet still more preferably 0.5 parts by weight to 50 parts by weight, yet even more preferably more than 0.5 parts by weight and less than 50 parts by weight, particularly preferably 0.8 parts by weight to 30 parts by weight, and most preferably more than 1 part by weight and 20 parts by weight or less with respect to 1 part by weight of the polymer containing a structural unit derived from acrylamide. That is, in a preferred embodiment of the medical device, the hydrophilic copolymer (2) is contained in the surface lubricious layer at a ratio of 0.5 parts by weight or more and less than 500 parts by weight (more preferably 0.5 parts by weight to 450 parts by weight, still more preferably 0.5 parts by weight to 350 parts by weight, even more preferably 0.5 parts by weight to 200 parts by weight, yet still more preferably 0.5 parts by weight to 50 parts by weight, yet even more preferably more than 0.5 parts by weight and less than 50 parts by weight, particularly preferably 0.8 parts by weight to 30 parts by weight, and most preferably more than 1 part by weight and 20 parts by weight or less) with respect to 1 part by weight of the polymer containing a structural unit derived from acrylamide. With such an abundance ratio (mixing ratio), the water retention effect of the polymer containing a structural unit derived from acrylamide and the lubricating property of the hydrophilic copolymer (2) can be exhibited in a good balance. Note that when the surface lubricious layer contains two or more types of polymers containing a structural unit derived from acrylamide, the above "1 part by weight" means that a total amount of these polymers containing a structural unit derived from acrylamide is 1 part by weight. Similarly, when the surface lubricious layer contains two or more types of hydrophilic copolymers (2), the above amount (part by weight) of the hydrophilic copolymer (2) means a total amount of these hydrophilic copolymers (2). The above abundance ratio (mixing ratio) is substantially equal to a ratio of a total charge amount (weight) of the hydrophilic copolymer (2) with respect to a total charge amount (weight) of the polymer containing a structural unit derived from acrylamide during formation of the surface lubricious layer.

Here, the presence and the ratio (composition) of the structural unit derived from each polymerizable monomer in the hydrophilic copolymer (2) and the presence of the polymer containing a structural unit derived from acrylamide in the surface lubricious layer can be confirmed by, for example, analyzing peak intensity of a group contained in each structural unit using a known method such as IR, NMR, and pyrolysis GC/MS. In the present description, the presence and the ratio (composition) of the structural unit derived from each polymerizable monomer in the hydrophilic copolymer (2) in the surface lubricious layer can be detected and measured by the same method as described above (Method for Detecting and Measuring Presence and Ratio of Structural Unit Derived from Each Polymerizable Monomer in Hydrophilic Copolymer (1) in Adhesive Layer). The polymer containing a structural unit derived from acrylamide in the surface lubricious layer can also be confirmed in the same manner as described above (Method for Detecting and Measuring Presence and Ratio of Structural Unit Derived from Each Polymerizable Monomer in Hydrophilic Copolymer (1) in Adhesive Layer). That is, in the above method, a peak specific to a site specific to the polymer containing a structural unit derived from acrylamide (for example, in $^{1}$H-NMR, a proton (hydrogen atom) of an amide group, or in $^{13C}$-NMR, a carbon atom adjacent to an amide group) is to be confirmed, and when these peaks can be confirmed, it is determined that the polymer containing a structural unit derived from acrylamide is present in the sample.

The abundance ratio (mixing ratio) of the hydrophilic copolymer (2) with respect to the polymer containing a structural unit derived from acrylamide in the surface lubricious layer can also be measured using the same known method as described above. In the present description, the abundance ratio (mixing ratio) of the hydrophilic copolymer (2) with respect to the polymer containing a structural unit derived from acrylamide in the surface lubricious layer is measured according to the following method.

(Method for Measuring Abundance Ratio (Mixing Ratio) of Hydrophilic Copolymer (2) with respect to Polymer Containing Structural Unit Derived from Acrylamide in Surface Lubricious Layer)

With the surface of the medical device swollen with heavy water or the like, precision diagonal cutting is performed on the medical device to prepare an inclined cross section of the medical device. From the cross section, a surface lubricious layer portion located near the surface of the medical device is cut, and a material of the surface lubricious layer portion is collected. Next, the material of the surface lubricious layer portion is filled into a sample tube for solid NMR without any gap to prepare a sample and NMR measurement is performed. Here, a concentration (concentration (c')) of a site (for example, a benzophenone group) specific to the structural unit (C') is measured. A concentration of the copolymer (concentration (c")) is calculated based on this concentration (c') and the composition of the hydrophilic copolymer (2). This concentration (c") is regarded as an amount of the hydrophilic copolymer (2) in the surface lubricious layer. Separately, in the same manner, a concentration of a site specific to the polymer containing a structural unit derived from acrylamide (for example, in $^{1}$H-NMR, a proton (hydrogen atom) of an amide group, or in $^{13}$C-NMR, a carbon atom adjacent to an amide group) (concentration (h)) is measured. This concentration (h) is regarded as an amount of the polymer containing a structural unit derived from acrylamide in the surface lubricious layer. A value obtained by dividing the concentration (c") by the concentration (h) (concentration (c")/concentration (h)) is the abundance ratio (mixing ratio) of the hydrophilic copolymer (2) with respect to the polymer containing a structural unit derived from acrylamide in the surface lubricious layer. Note that an analyzer and measurement conditions used in the above measurement are as follows.

Analyzer: NM080006, manufactured by JEOL Ltd.

Measurement conditions: heavy water or a mixed liquid of heavy water and a heavy solvent of a lower alcohol.

Hereinafter, each polymerizable monomer constituting the hydrophilic copolymer (2) contained in the surface lubricious layer according to the disclosure will be described.

(Polymerizable Monomer (A'))

The hydrophilic copolymer (2) contains the structural unit derived from the polymerizable monomer (A') having a sulfobetaine structure (structural unit (A')). Here, the structural unit (A') constituting the hydrophilic copolymer (2) may be one type alone or a combination of two or more types. That is, the structural unit (A') may be constituted by only one type of structural unit (A'), or may be constituted by two or more types of structural units (A'). Note that a plurality of structural units (A') may be present in a block shape or in a random shape.

The polymerizable monomer (A') (monomer A') is a polymerizable monomer having a sulfobetaine structure. The sulfobetaine structure included in the structural unit derived from the monomer A' is excellent in effect of imparting the lubricating property. Therefore, the hydrophilic copolymer (2) containing the structural unit derived from the monomer A' is considered to be excellent in lubricating property. A homopolymer of the monomer A' is soluble in an aqueous NaCl solution, but is insoluble or difficult to dissolve in water or a lower alcohol. Therefore, it is suggested that the sulfobetaine structure may have a strong electrostatic interaction. Therefore, a strong cohesive force acts inside the surface lubricious layer containing the hydrophilic copolymer according to the disclosure. Accordingly, the surface lubricious layer is considered to have high strength (excellent in durability). Note that the above is theory, and the invention is not limited to the above theory.

Since a specific definition and examples of the polymerizable monomer (A') are the same as those (of Polymerizable Monomer (A)) in the above adhesive layer, description thereof will be omitted here.

From the viewpoint of further improving the lubricating property and the durability (lubrication retaining property), the monomer A' is preferably a compound represented by the above formula (1). That is, in a preferred embodiment of the medical device, the polymerizable monomer (A') is a compound represented by the above formula (1).

(Polymerizable Monomer (B'))

The hydrophilic copolymer (2) contains the structural unit derived from the polymerizable monomer (B') having at least one group selected from the group consisting of a sulfonic acid group (—$SO_3H$), a sulfuric acid group (—$OSO_3H$), a sulfurous acid group (—$OSO_2H$), and salt groups thereof (structural unit (B')). Here, the structural unit (B') constituting the hydrophilic copolymer (2) may be one type alone or a combination of two or more types. That is, the structural unit (B') may be constituted by only one type of structural unit (B'), or may be constituted by two or more types of structural units (B'). Note that a plurality of structural units (B') may be present in a block shape or in a random shape.

The polymerizable monomer (B') (monomer B') is a polymerizable monomer having at least one group selected from the group consisting of a sulfonic acid group (—$SO_3H$), a sulfuric acid group (—$OSO_3H$), a sulfurous acid group (—$OSO_2H$), and salt groups thereof. By introducing such a group, anionization occurs in an aqueous solvent, and electrostatic repulsion occurs between the hydrophilic copolymers. As a result, an electrostatic interaction between the sulfobetaine structures and a hydrophobic interaction between the photoreactive groups in the hydrophilic copolymers are reduced. Therefore, the solvent solubility of the copolymer (particularly the solubility in water, a lower alcohol, or a mixed solvent of water and a lower alcohol) is improved. This improving effect is particularly remarkable when the photoreactive group of the monomer C' is a benzophenone group. Since the benzophenone group has a plurality of aromatic rings, the benzophenone groups are likely to associate with each other by a π-π interaction, which makes the polymers containing the benzophenone group to aggregate and insolubilize. Therefore, it is considered that by introducing the structural unit derived from the polymerizable monomer (B'), the electrostatic repulsion occurs as described above, and the association between the benzophenone groups is reduced, and thus the solubility or dispersibility of the polymer is rapidly improved. Note that the above mechanism is theory, and the invention is not limited to the above theory. Alternatively, even when the monomer C' has an ester group, the above improving effect can be obtained satisfactorily.

Since a specific definition and examples of the polymerizable monomer (B') are the same as those (of Polymerizable Monomer (B)) in the above adhesive layer, description thereof will be omitted here.

Among these, from the viewpoint of further improving the solvent solubility, the polymerizable monomer (B') is preferably a compound represented by the following formula (2), (3), or (4), and more preferably a compound represented by the following formula (2). That is, in a preferred embodiment of the medical device, the polymerizable monomer (B') is a compound represented by the following formula (2), (3), or (4). In a more preferred embodiment of the medical device, the polymerizable monomer (B') is a compound represented by the following formula (2). Note that since specific definitions of the formulas (2) to (4) are the same as those (of Polymerizable Monomer (B)) described above, description thereof will be omitted here.

[Chem. 7]

(2)

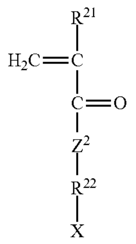

In the above formula (2), $R^{21}$ represents a hydrogen atom or a methyl group, $Z^2$ represents an oxygen atom or —NH—, $R^{22}$ represents a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

[Chem. 8]

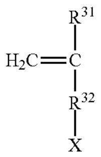

(3)

In the above formula (3), $R^{31}$ represents a hydrogen atom or a methyl group, $R^{32}$ represents a single bond or a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

[Chem. 9]

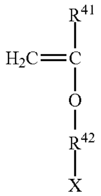

(4)

In the above formula (4), $R^{41}$ represents a hydrogen atom or a methyl group, $R^{42}$ represents a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof.

(Polymerizable Monomer (C'))

The hydrophilic copolymer (2) contains the structural unit derived from the polymerizable monomer (C') having a photoreactive group (structural unit (C')). Here, the structural unit (C') constituting the hydrophilic copolymer (2) may be one type alone or a combination of two or more types. That is, the structural unit (C') may be constituted by only one type of structural unit (C'), or may be constituted by two or more types of structural units (C'). Note that a plurality of structural units (C') may be present in a block shape or in a random shape.

The polymerizable monomer (C') (monomer C') is a polymerizable monomer having a photoreactive group. With the polymer monomer C', the surface lubricious layer containing the hydrophilic copolymer (2) can be firmly immobilized on the substrate layer via the adhesive layer. Therefore, the medical device can exhibit sufficient durability (lubrication retaining property).

Since a specific definition and examples of the polymerizable monomer (C') are the same as those (of Polymerizable Monomer (C)) in the above adhesive layer, description thereof will be omitted here.

From the viewpoints of forming a covalent bond with the adhesive layer and firm immobilization on the substrate layer, the photoreactive group of the polymerizable monomer (C') is preferably the same as the photoreactive group of the polymerizable monomer (C) in the hydrophilic copolymer (1) contained in the adhesive layer. That is, in a preferred embodiment of the medical device, the polymerizable monomer (C') has a group having a benzophenone structure.

The hydrophilic copolymer (2) may contain a structural unit derived from a polymerizable monomer other than the above monomer A', monomer B', and monomer C' (hereinafter, also referred to as "other monomer") in a range that does not impair the effects of the medical device. In the hydrophilic copolymer (2) according to the disclosure, a content of the structural unit derived from the other monomer is preferably less than 10 mol %, more preferably less than 5 mol %, and still more preferably less than 1 mol % (lower limit: more than 0 mol %), with respect to 100 mol %, which is the total of the structural units derived from all the monomers. Note that when the structural unit derived from the other monomer is constituted by two or more types of structural units, a composition of the above structural unit derived from the other monomer occupies a ratio (molar ratio (mol %)) of all the structural units derived from the other monomer with respect to the total of the structural units derived from all the monomers (100 mol %). Preferably, the hydrophilic copolymer (2) according to the disclosure is constituted only by the monomer A', the monomer B', and the monomer C' (the composition of the other monomer=0 mol %). Note that the mol % is substantially equivalent to a ratio of a charge amount (mol) of the other monomer with respect to the total charge amount (mol) of all the monomers in the production of the polymer.

A terminal end of the hydrophilic copolymer (2) is not particularly limited and is appropriately defined depending on types of raw materials to be used, and is usually a hydrogen atom. A structure of the copolymer is not particularly limited, and may be any of a random copolymer, an alternating copolymer, a periodic copolymer, and a block copolymer.

A weight average molecular weight (Mw) of the hydrophilic copolymer (2) is preferably several thousand to several million, more preferably 1,000 to 1,000,000, and particularly preferably 5,000 to 500,000. In the disclosure, the "weight average molecular weight" shall be a value measured by gel permeation chromatography (GPC) using polyethylene glycol as a standard substance.

[Method for Manufacturing Hydrophilic Copolymer (2)]

A method for manufacturing the hydrophilic copolymer (2) is not particularly limited, and specific description thereof is the same as that in the [Method for Manufacturing Hydrophilic Copolymer (1)] in the above adhesive layer, and thus the description is omitted here.

[Method for Manufacturing Medical Device]

A method for manufacturing the medical device according to the disclosure is not particularly limited except that the adhesive layer is formed using the above hydrophilic copolymer (1) and the surface lubricious layer is formed using the above hydrophilic copolymer (2) and polymer containing a structural unit derived from acrylamide, and a known method can be applied in the same manner or after appropriate modification. For example, preferred is a method in which a coating liquid is prepared by dissolving the hydrophilic copolymer (1) in a solvent, and is coated onto a substrate layer of the medical device to form an adhesive layer, and then a coating liquid is prepared by dissolving the hydrophilic copolymer (2) and the polymer containing a structural unit derived from acrylamide in a solvent, and is coated onto the above adhesive layer to form a surface lubricious layer. That is, the disclosure also provides the method for manufacturing the medical device. The method includes coating a coating liquid (1) containing the hydrophilic copolymer (1) onto the substrate layer to form an adhesive layer, and coating a coating liquid (2) containing the polymer containing a structural unit derived from acrylamide and the hydrophilic copolymer (2) onto the adhesive layer to form a surface lubricious layer. With such a method, the lubricating property and the durability (lubrication retaining property) can be imparted to the surface of the medical device.

(Coating Step for Adhesive Layer)

In the above method, the solvent used for dissolving the hydrophilic copolymer (1) is preferably water, a lower alcohol, or a mixed solvent of water and a lower alcohol from the viewpoints of working safety (low toxicity) and solubility. Here, the lower alcohol refers to a primary alcohol having 1 to 3 carbon atoms, that is, methanol, ethanol, n-propanol, or isopropanol. The above lower alcohols may be used alone or in combination of two or more types thereof.

A concentration of the hydrophilic copolymer (1) in the coating liquid (1) is not particularly limited, and is preferably 0.01 wt % to 50 wt %, more preferably 0.05 wt % to 40 wt %, and still more preferably 0.1 wt % to 30 wt %. Within such a range, coatability of the coating liquid (1) is good, and the obtained adhesive layer has sufficient lubricating property and durability (lubrication retaining property). A uniform adhesive layer having a desired thickness can be easily obtained with single coating. Therefore, the hydrophilic copolymer (1) can form a strong and uniform chemical bond with the substrate layer by subsequent irradiation with active energy rays (immobilizing step for adhesive layer). The range is also preferred in terms of production efficiency. Note that when the concentration of the hydrophilic copolymer (1) is less than 0.01 wt %, a sufficient amount of the hydrophilic copolymer (1) may not be immobilized on the surface of the substrate layer. When the concentration of the hydrophilic copolymer (1) is more than 50 wt %, the viscosity of the coating liquid (1) may become too high to obtain the adhesive layer having a uniform thickness. However, even when the concentration deviates from the above range, the coating liquid (1) can be sufficiently used as long as the function and effect of the medical device are not influenced.

A coating amount of the coating liquid (1) is not particularly limited, and is preferably an amount that corresponds to the thickness of the above adhesive layer.

Before coating the coating liquid (1), the surface of the substrate layer may be treated in advance by an ultraviolet irradiation treatment, a plasma treatment, a corona discharge treatment, a flame treatment, an oxidation treatment, a silane coupling treatment, a phosphoric acid coupling treatment, or the like. When the solvent of the coating liquid (1) is only water, it is difficult to coat the coating liquid (1) onto the surface of the hydrophobic substrate layer, and the surface of the substrate layer is made hydrophilic by performing a plasma treatment on the surface of the substrate layer. Accordingly, wettability of the coating liquid (1) to the surface of the substrate layer is improved, and a uniform adhesive layer can be formed. By applying the above treatment to the surface of the substrate layer, which does not have any C—H bond of a metal, a fluorine resin, or the like, a covalent bond with the photoreactive group of the hydrophilic copolymer (1) can be formed.

A method for coating the coating liquid (1) onto the surface of the substrate layer is not particularly limited, and a known method in the related art can be applied, such as a coating printing method, a dipping method (dipping method, dip coating method), a spraying method (spray method), a spin coating method, and a mixed solution impregnated sponge coating method. Among these, a dipping method (dipping method, dip coating method) is preferred.

(Drying Step for Adhesive Layer)

It is preferable that, after coating the coating liquid (1) containing the hydrophilic copolymer (1) according to the disclosure onto the surface of the substrate layer as described above, the substrate layer is taken out from the coating liquid (1), and a coating film is dried. Drying conditions are not particularly limited as long as the solvent can be removed from the coating film, and a warm air treatment may be performed using a dryer or the like, or natural drying may be performed. A pressure condition during the drying is also not limited at all, and the drying may be performed under a normal pressure (atmospheric pressure), or under a pressure or a reduced pressure. As a drying unit (device), for example, an oven, a decompression dryer, or the like can be used, and in the case of natural drying, no drying unit (device) is particularly required.

(Immobilizing Step for Adhesive Layer)

The coating film after the above drying step is irradiated with active energy rays. Accordingly, the photoreactive group in the coating film (the monomer C of the hydrophilic copolymer (1)) is activated, and a chemical bond is formed between the photoreactive group and an alkyl group (hydrocarbon group) contained in the substrate layer. More specifically, a case of a combination of the photoreactive group having a benzophenone structure and a resin (a material having a hydrocarbon group) constituting the substrate layer will be described. When the hydrophilic copolymer (1) has the photoreactive group having a benzophenone structure, two radicals are generated in the photoreactive group by irradiation with ultraviolet rays. One of these radicals abstracts the hydrogen atom from the alkyl group (hydrocarbon group) in the resin, and instead one radical is generated in the material. Then, the remaining radical in the photoreactive group and the radical generated in the material are bonded to each other, whereby a covalent bond is formed between the photoreactive group of the hydrophilic copolymer (1) in the adhesive layer and the material (resin) in the substrate layer. With such a chemical bond, the adhesive layer containing the hydrophilic copolymer (1) is firmly immobilized on the substrate layer. Therefore, the adhesive layer can exhibit sufficient durability (lubrication retaining property).

Examples of the active energy rays include ultraviolet rays (UV), electron beams, and gamma rays, and are preferably ultraviolet rays or electron beams, and more preferably ultraviolet rays in consideration of an influence on a human body. When the active energy rays are ultraviolet rays, a wavelength at which the photoreactive group can be activated can be appropriately selected as an irradiation wavelength. Specifically, a wavelength range of the ultraviolet rays is preferably 200 nm to 400 nm, and more preferably 220 nm to 390 nm. The irradiation with ultraviolet rays is preferably performed under a temperature condition of 10° C. to 100° C., and more preferably 20° C. to 80° C. An irradiation intensity of the ultraviolet rays is not particularly limited, and is preferably 1 $mW/cm^2$ to 5000 $mW/cm^2$, more preferably 10 $mW/cm^2$ to 1000 $mW/cm^2$, and still more preferably 50 $mW/cm^2$ to 500 $mW/cm^2$. An integrated light amount of the ultraviolet rays (an integrated light amount of the ultraviolet rays on the adhesive layer before coating the surface lubricious layer) is not particularly limited, and is preferably 100 $mJ/cm^2$ to 100,000 $mJ/cm^2$, and more preferably 500 $mJ/cm^2$ to 50,000 $mJ/cm^2$. Examples of a device for emitting the ultraviolet rays include a high-pressure mercury lamp, a low-pressure mercury lamp, a metal halide lamp, a xenon lamp, and a halogen lamp. Note that a method for emitting the active energy rays is not particularly limited, and the irradiation may be performed from one direction, or from multiple directions, or the irradiation may be performed while rotating an irradiation source, or while rotating an object to be irradiated (one in which the coating film of the adhesive layer is formed on the substrate layer).

After performing the above irradiation with active energy rays, the coating film may be washed with a solvent (for example, the solvent used for preparing the coating liquid (1)) to remove the unreacted hydrophilic copolymer (1).

The immobilization of the coating film (adhesive layer) on the substrate layer can be confirmed by using a known analytical method such as FT-IR, XPS, and TOF-SIMS. For example, the immobilization can be confirmed by performing FT-IR measurement before and after the irradiation with active energy rays and comparing ratios of a peak of bonds formed by the irradiation with active energy rays with respect to a peak of invariant bonds.

With the above method, in the medical device according to the disclosure, the adhesive layer containing the hydrophilic copolymer (1) is formed on the surface of the substrate layer.

(Coating Step for Surface Lubricious Layer)

Here, the hydrophilic copolymer (2) and the polymer containing a structural unit derived from acrylamide are dissolved in a solvent to prepare the coating liquid (2), and the coating liquid (2) is coated onto the adhesive layer formed as above. In the above method, the solvent used for dissolving the hydrophilic copolymer (2) and the polymer containing a structural unit derived from acrylamide is preferably water, a lower alcohol, or a mixed solvent of water and a lower alcohol from the viewpoints of working safety (low toxicity) and solubility. Here, the lower alcohol refers to a primary alcohol having 1 to 3 carbon atoms, that is, methanol, ethanol, n-propanol, or isopropanol. The above lower alcohols may be used alone or in combination of two or more types thereof. Here, the hydrophilic copolymer (2) and the polymer containing a structural unit derived from acrylamide may be added to the solvent together, may be sequentially added to the same solvent (the hydrophilic copolymer (2) and then the polymer containing a structural unit derived from acrylamide, or the polymer containing a structural unit derived from acrylamide and then the hydrophilic copolymer (2)), or the hydrophilic copolymer (2) and the polymer containing a structural unit derived from acrylamide may be dissolved in different solvents and then mixed with each other. Note that when the hydrophilic copolymer (2) and the polymer containing a structural unit derived from acrylamide may be dissolved in different solvents, the solvents may be the same as or different from each other, and are preferably the same in consideration of ease of operation and the like.

A concentration of the hydrophilic copolymer (2) in the coating liquid (2) is not particularly limited, and is preferably more than 0.05 wt % and less than 5 wt %, more preferably 0.1 wt % to 2.5 wt %, and particularly preferably 0.1 wt % to 1.0 wt %. Within such a range, coatability of the coating liquid (2) is good, and a strong and uniform chemical bond can be formed with the adhesive layer (hydrophilic copolymer (1)) or the polymer containing a structural unit derived from acrylamide by subsequent irradiation with active energy rays (immobilizing step for surface lubricious layer) (therefore, the surface lubricious layer has excellent lubricating property and durability (lubrication retaining property)). The range is also preferred in terms of production efficiency. A concentration of the polymer containing a structural unit derived from acrylamide in the coating liquid (2) is not particularly limited, and is preferably more than 0.001 wt % and less than 5 wt %, more preferably 0.003 wt % to 3 wt %, still more preferably 0.007 wt % to 0.5 wt %, even more preferably more than 0.01 wt % and less than 0.5 wt %, and particularly preferably 0.03 wt % to 0.3 wt %. Within such a range, the coatability of the coating liquid (2) is good, and the obtained surface lubricious layer can exhibit a sufficient water retention effect (therefore, the surface lubricious layer can exhibit an excellent lubricating property even under a high load condition). Here, a mixing ratio of the hydrophilic copolymer (2) with respect to the polymer containing a structural unit derived from acrylamide in the coating liquid (2) is not particularly limited, and is preferably the same mixing ratio as described in the section of Surface Lubricious Layer.

A coating amount of the coating liquid (2) is not particularly limited, and is preferably an amount that corresponds to the thickness of the above surface lubricious layer.

A method for coating the coating liquid (2) onto the surface of the adhesive layer is not particularly limited, and a known method in the related art can be applied, such as a coating printing method, a dipping method (dipping method, dip coating method), a spraying method (spray method), a spin coating method, and a mixed solution impregnated sponge coating method. Among these, a dipping method (dipping method, dip coating method) is preferred.

(Drying Step for Surface Lubricious Layer)

As described above, it is preferable that, after immersing the substrate layer on which the adhesive layer is formed in advance in the coating liquid (2), the substrate layer is taken out from the coating liquid (2) and a coating film is dried. Drying conditions are not particularly limited as long as the solvent can be removed from the coating film, and a warm air treatment may be performed using a dryer or the like, or natural drying may be performed. A pressure condition during the drying is also not limited at all, and the drying may be performed under a normal pressure (atmospheric pressure), or under a pressure or a reduced pressure. As a drying unit (device), for example, an oven, a decompression dryer, or the like can be used, and in the case of natural drying, no drying unit (device) is particularly required.

(Immobilizing Step for Surface Lubricious Layer)

The coating film after the above drying step is irradiated with active energy rays. Accordingly, the photoreactive group of the hydrophilic copolymer (1) (monomer C) in the adhesive layer and the photoreactive group of the hydrophilic copolymer (2) (monomer C') in the surface lubricious layer are activated, and a chemical bond is formed between the photoreactive group of the hydrophilic copolymer (1) and the photoreactive group of the hydrophilic copolymer (2) and the polymer containing a structural unit derived from acrylamide. For example, a case of a combination of the photoreactive group having a benzophenone structure of the hydrophilic copolymer (1) in the adhesive layer and the photoreactive group having a benzophenone structure of the hydrophilic copolymer (2) and the polymer containing a structural unit derived from acrylamide in the surface lubricious layer will be described. When the hydrophilic copolymers (1) and (2) have the photoreactive group having a benzophenone structure, two radicals are generated in the photoreactive group of each hydrophilic copolymer by the irradiation with ultraviolet rays. One of these radicals abstracts the hydrogen atom from an alkyl group (hydrocarbon group) in the polymer containing a structural unit derived from acrylamide, and instead one radical is generated in the polymer containing a structural unit derived from acrylamide. Then, the remaining radical in the photoreactive group and the radical generated in the polymer containing a structural unit derived from acrylamide are bonded to each other, whereby a covalent bond is formed between the photoreactive group of the hydrophilic copolymer (1) in the adhesive layer and the polymer containing a structural unit derived from acrylamide in the surface lubricious layer, or between the photoreactive group of the hydrophilic copolymer (2) and the polymer containing a structural unit derived from acrylamide in the surface lubricious layer. With such a chemical bond between the polymer containing a structural unit derived from acrylamide and the hydrophilic copolymer in the adhesive layer or the surface lubricious layer, the surface lubricious layer is firmly immobilized on the adhesive layer, and at the same time, the polymer containing a structural unit derived from acrylamide is firmly immobilized in the surface lubricious layer. In addition, one of the two radicals of the hydrophilic copolymer (1) generated by the irradiation with the ultraviolet rays abstracts the hydrogen atom from an alkyl group (hydrocarbon group) in the hydrophilic copolymer (2), and instead one radical is generated in the hydrophilic copolymer (2). Then, the remaining radical in the photoreactive group of the hydrophilic copolymer (1) and the radical generated in the hydrophilic copolymer (2) are bonded to each other, whereby a covalent bond is formed between the photoreactive group of the hydrophilic copolymer (1) in the adhesive layer and the hydrophilic copolymer (2) in the surface lubricious layer. Similarly, one of the two radicals of the hydrophilic copolymer (2) generated by the irradiation with the ultraviolet rays abstracts the hydrogen atom from an alkyl group (hydrocarbon group) in the hydrophilic copolymer (1), and instead one radical is generated in the hydrophilic copolymer (1). Then, the remaining radical in the photoreactive group of the hydrophilic copolymer (2) and the radical generated in the hydrophilic copolymer (1) are bonded to each other, whereby a covalent bond is formed between the photoreactive group of the hydrophilic copolymer (1) in the adhesive layer and the hydrophilic copolymer (2) in the surface lubricious layer. With such a chemical bond between the hydrophilic copolymer (1) in the adhesive layer and the hydrophilic copolymer (2) in the surface lubricious layer, the surface lubricious layer is also firmly immobilized on the adhesive layer. Therefore, the surface lubricious layer can effectively exhibit the water retention effect of the polymer containing a structural unit derived from acrylamide and can exhibit an excellent lubricating property. The water retention effect of the polymer containing a structural unit derived from acrylamide can be maintained for a long period of time, and the excellent durability (lubrication retaining property) can also be exhibited.

Examples of the active energy rays include ultraviolet rays (UV), electron beams, and gamma rays, and are preferably ultraviolet rays or electron beams, and more preferably ultraviolet rays in consideration of an influence on a human body. When the active energy rays are ultraviolet rays, a wavelength at which the photoreactive group can be activated can be appropriately selected as an irradiation wavelength. Specifically, a wavelength range of the ultraviolet rays is preferably 200 nm to 400 nm, and more preferably 220 nm to 390 nm. The irradiation with ultraviolet rays is preferably performed under a temperature condition of 10° C. to 100° C., and more preferably 20° C. to 80° C. An irradiation intensity of the ultraviolet rays is not particularly limited, and is preferably 1 $mW/cm^2$ to 5000 $mW/cm^2$, more preferably 10 $mW/cm^2$ to 1000 $mW/cm^2$, and still more preferably 50 $mW/cm^2$ to 500 $mW/cm^2$. An integrated light amount of the ultraviolet rays (an integrated light amount of the ultraviolet rays on the surface lubricious layer) is not particularly limited, and is preferably 100 $mJ/cm^2$ to 100,000 $mJ/cm^2$, and more preferably 500 $mJ/cm^2$ to 50,000 $mJ/cm^2$. Examples of a device for emitting the ultraviolet rays include a high-pressure mercury lamp, a low-pressure mercury lamp, a metal halide lamp, a xenon lamp, and a halogen lamp. Note that a method for emitting the active energy rays is not particularly limited, and the irradiation may be performed from one direction, or from multiple directions, or the irradiation may be performed while rotating an irradiation source, or while rotating an object to be irradiated (one in which the coating film of the adhesive layer is formed on the substrate layer).

After performing the above irradiation with active energy rays, the coating film may be washed with a solvent (for example, the solvent used for preparing the coating liquid (2)) to remove the unreacted hydrophilic copolymer (2).

The immobilization of the coating film (surface lubricious layer) on the adhesive layer can be confirmed by using a known analytical method such as FT-IR, XPS, and TOF-SIMS. For example, the immobilization can be confirmed by performing FT-IR measurement before and after the irradiation with active energy rays and comparing ratios of a peak of bonds formed by the irradiation with active energy rays with respect to a peak of invariant bonds.

With the above method, in the medical device according to the disclosure, the surface lubricious layer containing the hydrophilic copolymer (2) and the polymer containing a structural unit derived from acrylamide is formed on the surface of the adhesive layer.

[Use of Medical Device]

The medical device disclosed here can be used in contact with a body fluid, blood, and the like. The surface thereof has a lubricating property in an aqueous liquid such as a body fluid or physiological saline, and can enhance operability and reduce damage to tissue mucosa. Specific examples include a catheter, a stent, and a guide wire to be used in blood vessels. That is, in one embodiment, the medical device is a catheter, a stent, or a guide wire. The medical device is also exemplified by the following.

(a) Catheters to be orally or nasally inserted or allowed to indwell in a digestive organ, such as stomach tube catheters, feeding catheters, and tubes for tube feeding.

(b) Catheters to be orally or nasally inserted or allowed to indwell in a respiratory tract or trachea, such as oxygen catheters, oxygen cannulas, tubes and cuffs of tracheal tubes, tubes and cuffs of tracheotomy tubes, and tracheal aspiration catheters.

(c) Catheters to be inserted or allowed to indwell in a urethra or ureter, such as urethra catheters, urinary catheters, and catheters and balloons of urethra balloon catheters.

(d) Catheters to be inserted or allowed to indwell in various lumens in living bodies, organs, and tissues, such as suction catheters, drain catheters, and rectum catheters.

(e) Catheters to be inserted or allowed to indwell in a blood vessel, such as indwelling needles, IVH catheters, thermodilution catheters, angiography catheters, vasodilation catheters, and dilators or introducers, or guide wires, stylets, and the like for the catheters.

(f) Artificial tracheae, artificial bronchi, and the like.

(g) Medical devices for extracorporeal circulation therapy (artificial lungs, artificial hearts, artificial kidneys, and the like) and circuits therefor.

EXAMPLES

Hereinafter, the invention will be specifically described with reference to Examples, but the invention is not limited to these Examples. Note that parts and % in Examples are all by weight. In the following examples, unless otherwise defined, conditions for allowing to stand at room temperature are all at 23° C. and 55% RH.

Production Example 1: Production of Hydrophilic Copolymer (A)

In 10 mL of a 2,2,2-trifluoroethanol/water (9/1 v/v) mixed solvent, 1.82 g (6.5 mmol) of [2-(methacryloyloxy)ethyl] dimethyl-(3-sulfopropyl)ammonium hydroxide (MSPB) manufactured by Sigma-Aldrich Co. LLC., 1.46 g (3.2 mmol) of a 50 wt % aqueous solution of sodium 2-acrylamide-2-methyl-1-propanesulfonate (AMPS(Na)) manufactured by Sigma-Aldrich Co. LLC., and 0.080 g (0.3 mmol) of 4-methacryloyloxybenzophenone (MBP) manufactured by MCC UNITECH Co., Ltd. were dissolved to prepare a reaction solution. Next, the reaction solution was charged into a 30 mL eggplant-shaped flask, oxygen was removed by sufficient nitrogen bubbling, 2.8 mg (0.010 mmol) of a polymerization initiator 4,4'-azobis(4-cyanovaleric acid) was added, followed by immediate sealing, and polymerization was carried out in a water bath at 75° C. for 3 hours. Next, the solution was subjected to reprecipitation in acetone, and the supernatant was removed by decantation to obtain a copolymer (A).

The composition of the obtained copolymer (A) was MSPB:AMPS(Na):MPB=65:32:3 in terms of mol %. Here, the obtained copolymer (A) corresponds to the hydrophilic copolymer (1) contained in the adhesive layer according to the disclosure and the hydrophilic copolymer (2) contained in the surface lubricious layer according to the disclosure. The weight average molecular weight (Mw) of the obtained copolymer (A) was measured by GPC, and was 180,000 in terms of polyethylene glycol.

Production Example 2: Production of Hydrophilic Copolymer (B)

In 10 mL of a 2,2,2-trifluoroethanol/water (9/1 v/v) mixed solvent, 1.99 g (6.5 mmol) of a [3-(methacryloylamino) propyl]dimethyl(3-sulfobutyl)ammonium hydroxide inner salt (MSBB) manufactured by FUJIFILM Wako Pure Chemical Cooperation, 1.46 g (3.2 mmol) of a 50 wt % aqueous solution of sodium 2-acrylamide-2-methyl-1-propanesulfonate (AMPS(Na)) manufactured by Sigma-Aldrich Co. LLC., and 0.080 g (0.3 mmol) of 4-methacryloyloxybenzophenone (MBP) manufactured by MCC UNITECH Co., Ltd. were dissolved to prepare a reaction solution. Next, the reaction solution was charged into a 30 mL eggplant-shaped flask, oxygen was removed by sufficient nitrogen bubbling, 2.8 mg (0.010 mmol) of a polymerization initiator 4,4'-azobis(4-cyanovaleric acid) was added, followed by immediate sealing, and polymerization was carried out in a water bath at 75° C. for 3 hours. Next, the solution was subjected to reprecipitation in acetone, and the supernatant was removed by decantation to obtain a copolymer (B).

The composition of the obtained copolymer (B) was MSBB:AMPS(Na):MPB=65:32:3 in terms of mol %. Here, the obtained copolymer (B) corresponds to the hydrophilic copolymer (1) contained in the adhesive layer according to the disclosure and the hydrophilic copolymer (2) contained in the surface lubricious layer according to the disclosure. The weight average molecular weight (Mw) of the obtained copolymer (B) was measured by GPC, and was 190,000 in terms of polyethylene glycol.

Example 1

The copolymer (A) obtained in Production Example 1 (corresponding to the hydrophilic copolymer (1) according to the disclosure) was dissolved in ethanol/water (3/7 w/w) so as to be 10 wt %, to prepare a coating liquid (1-A). Next, a polyamide tube (having an outer diameter of 2.4 mm and a length of 70 mm) was dipped in the coating liquid (1-A), and was taken out at a rate of 1 mm/sec. Next, the polyamide tube was dried at room temperature for 60 seconds to remove the solvent. Next, the polyamide tube was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form an adhesive layer on the polyamide tube (polyamide tube (1-A)). Note that as a UV irradiation device, ECE2000 (high pressure mercury lamp) manufactured by Dymax Corporation was used.

Next, polyacrylamide manufactured by Sigma-Aldrich Co. LLC. (number average molecular weight (Mn)=150,000) was dissolved in water so as to be 0.1 wt % and the copolymer (A) obtained in Production Example 1 (corresponding to the hydrophilic copolymer (2) according to the disclosure) was dissolved in water so as to be 1 wt %, to prepare a coating liquid (1'). A mixing ratio (weight ratio) of polyacrylamide to the hydrophilic copolymer (2) in the coating liquid (1') is 1:10. Next, the polyamide tube (1-A) prepared above was dipped in the coating liquid (1') and was taken out at a rate of 5 mm/sec. Next, the polyamide tube (1-A) was dried at room temperature for 60 seconds to remove the solvent. Next, the polyamide tube (1-A) was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form a surface lubricious layer on the adhesive layer of the polyamide tube (1-A) (polyamide tube (1')). Note that as a UV irradiation device, ECE2000 (high pressure mercury lamp) manufactured by Dymax Corporation was used. A mixing ratio (weight ratio) of polyacrylamide to the hydrophilic copolymer (2) in the surface lubricious layer of the polyamide tube (1') is 1:10.

Next, the obtained polyamide tube (1') was evaluated for the lubricating property and durability (lubrication retaining property) using a friction meter (Handy Tribo Master TL201 manufactured by Trinity-Lab Inc.) 20 shown in FIG. 3 according to the following method. Results are shown in FIG. 4.

That is, a core material 18 was inserted into the above sample (polyamide tube (1')) to prepare a sample 16. The sample 16 was laid down in a length direction and fixed in a petri dish 12, and was immersed in physiological saline 17 having a depth that the entire sample 16 was immersed in the physiological saline. The petri dish 12 was placed on a moving table 15 of the friction meter 20 shown in FIG. 3. A silicon terminal (diameter: 10 mm) 13 was brought into contact with the sample 16, and a load 14 of 450 g was applied onto the terminal. While the moving table 15 was subjected to 10 horizontal reciprocations under a sliding distance set to 25 mm and a sliding rate set to 16.7 mm/sec, a sliding resistance value (gf) was measured. During the reciprocations from the first time to 10th time, an average of the sliding resistance values on a forward way for each reciprocation was taken and plotted on a graph as a test force to thereby evaluate a variation in sliding resistance value during the 10 repeated slides.

Comparative Example 1

The copolymer (A) obtained in Production Example 1 (corresponding to the hydrophilic copolymer (1) according to the disclosure) was dissolved in ethanol/water (3/7 w/w) so as to be 10 wt %, to prepare a coating liquid (1-A). Next, a polyamide tube (having an outer diameter of 2.4 mm and a length of 70 mm) was dipped in the coating liquid (1-A), and was taken out at a rate of 1 mm/sec. Next, the polyamide tube was dried at room temperature for 60 seconds to remove the solvent. Next, the polyamide tube was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form a copolymer layer on the polyamide tube (comparative polyamide tube (1)). Note that as a UV irradiation device, ECE2000 (high pressure mercury lamp) manufactured by Dymax Corporation was used. The comparative polyamide tube (1) has the same structure as the polyamide tube (1') in Example 1 except that the surface lubricious layer does not exist.

Next, the obtained comparative polyamide tube (1) was evaluated for the lubricating property and the durability (lubrication retaining property) in the same manner as in Example 1. Results are shown in FIG. 4.

According to FIG. 4, the polyamide tube (1') according to the disclosure has a low initial (the first reciprocation) sliding resistance value (excellent in lubricating property), and the sliding resistance value thereof hardly changes until the 10th reciprocation (excellent in durability (lubrication retaining property)). In contrast, the comparative polyamide tube (1) is excellent in durability (lubrication retaining property), but an initial sliding resistance value thereof is higher than that of the polyamide tube (1') according to the disclosure. This evaluation method is a method on assumption of a high load condition where a clearance between a catheter and an inner surface of a lumen in a living body is small. That is, the sliding resistance value is measured using the tube as a sample. The tube-shaped sample has a contact area with the terminal smaller than that of a sheet-shaped sample. Therefore, the tube-shaped sample has a force per unit area applied from the terminal (a larger load) larger than that of the sheet-shaped sample. Therefore, it is considered that the medical device according to the disclosure can exhibit excellent lubricating property and durability (lubrication retaining property) even under a high load condition where the clearance between the catheter and the inner surface of the lumen in the living body is small. Note that although the comparative polyamide tube (1) in Comparative Example 1 has a sliding resistance value at an initial stage (the first reciprocation) and up to the 10th reciprocation higher than that of the polyamide tube (1') according to the disclosure, it is considered that the comparative polyamide tube (1) also exhibits sufficient lubricating property and durability (lubrication retaining property) under normal conditions.

Examples 2 to 6

Polyacrylamide manufactured by Sigma-Aldrich Co. LLC. (number average molecular weight (Mn)=150,000) was dissolved in water so as to be 0.1 wt %, and the copolymer (A) obtained in Production Example 1 (corresponding to the hydrophilic copolymer (2) according to the disclosure) was dissolved in water so as to be 5 wt % (coating liquid (2')), 2.5 wt % (coating liquid (3')), 0.5 wt % (coating liquid (4')), 0.1 wt % (coating liquid (5')), and 0.05 wt % (coating liquid (6')), to prepare coating liquids (2') to (6'). Mixing ratios (weight ratios) of polyacrylamide to the hydrophilic copolymer (2) in the coating liquids (2') to (6') are 1:50, 1:25, 1:5, 1:1, and 1:0.5, respectively.

Polyamide tubes (2') to (6') were prepared in the same manner as in Example 1 except that the coating liquids (2') to (6') prepared above were used instead of the coating liquid (1') in Example 1. Here, mixing ratios (weight ratios) of polyacrylamide to the hydrophilic copolymer (2) in the surface lubricious layer of the polyamide tubes (2') to (6') are 1:50, 1:25, 1:5, 1:1, and 1:0.5, respectively.

Next, the lubricating property (the sliding resistance value at the first reciprocation) of the obtained polyamide tubes (2') to (6') was evaluated in the same manner as in Example 1. Results are shown in the following Table 1. Note that in the following Table 1, the results of Comparative Example 1 are also shown. Evaluation criteria in the following Table 1 are as follows. The lubricating property (the sliding resistance value at the first reciprocation) in Table 1 shows results when the number of samples is 2 (n=2). When both samples are A, the lubricating property (the sliding resistance value at the first reciprocation) is indicated as "A", and when one sample is A and the other sample is B, the lubricating property (the sliding resistance value at the first reciprocation) is indicated as "B to A".

(Evaluation Criteria)

A: The sliding resistance value at the first reciprocation is less than 40% of that of Comparative Example 1.

B: The sliding resistance value at the first reciprocation is 40% or more and less than 60% of that of Comparative Example 1.

C: The sliding resistance value at the first reciprocation is 60% or more and less than 90% of that of Comparative Example 1.

D: The sliding resistance value at the first reciprocation is 90% or more of that of Comparative Example 1.

TABLE 1

(Concentration of polyacrylamide: 0.1 wt %)

| Concentration (wt %) of hydrophilic copolymer (2) | Mixing ratio (weight ratio) of polyacrylamide: hydrophilic copolymer (2) in surface lubricious layer | Lubricating property (sliding resistance value at first reciprocation) |
|---|---|---|
| 5 | 1:50 | C |
| 2.5 | 1:25 | B |
| 1 | 1:10 | A |
| 0.5 | 1:5 | A |
| 0.1 | 1:1 | B to A |
| 0.05 | 1:0.5 | C |
| — | Comparative Example 1 | D |

Examples 7 to 9

The copolymer (A) obtained in Production Example 1 (corresponding to the hydrophilic copolymer (2) according to the disclosure) was dissolved in water so as to be 1 wt %, and polyacrylamide manufactured by Sigma-Aldrich Co. LLC. (number average molecular weight (Mn)=150,000) was dissolved in water so as to be 0.01 wt % (coating liquid (7')), 0.05 wt % (coating liquid (8')), and 1 wt % (coating liquid (9')), to prepare coating liquids (7') to (9'). Mixing ratios (weight ratios) of polyacrylamide to the hydrophilic copolymer (2) in the coating liquids (7') to (9') are 1:100, 1:20, and 1:1, respectively.

Polyamide tubes (7') to (9') were prepared in the same manner as in Example 1 except that the coating liquids (7') to (9') prepared above were used instead of the coating liquid (1') in Example 1. Here, mixing ratios (weight ratios) of polyacrylamide to the hydrophilic copolymer (2) in the surface lubricious layer of the polyamide tubes (7') to (9') are 1:100, 1:20, and 1:1, respectively.

Next, the lubricating property (the sliding resistance value at the first reciprocation) of the obtained polyamide tubes (7') to (9') was evaluated in the same manner as in Example 1. Results are shown in the following Table 2. Note that in the following Table 2, the results of Comparative Example 1 are also shown. Evaluation criteria in the following Table 2 are the same as those in Table 1.

TABLE 2

(Concentration of hydrophilic copolymer (2): 1 wt %)

| Concentration (wt %) of polyacrylamide | Mixing ratio (weight ratio) of polyacrylamide:hydrophilic surface lubricious layer | Lubricating property (sliding copolymer (2) in resistance value at first reciprocation) |
|---|---|---|
| 0.01 | 1:100 | C |
| 0.05 | 1:20 | A |
| 0.1 | 1:10 | A |
| 1 | 1:1 | B |
| — | Comparative Example 1 | D |

Example 10

Polyacrylamide manufactured by Sigma-Aldrich Co. LLC. (number average molecular weight (Mn)=40,000) was dissolved in water so as to be 0.1 wt % and the copolymer (A) obtained in Production Example 1 (corresponding to the hydrophilic copolymer (2) according to the disclosure) was dissolved in water so as to be 1 wt %, to prepare a coating liquid (10'). A mixing ratio (weight ratio) of polyacrylamide to the hydrophilic copolymer (2) in the coating liquid (10') is 1:10.

A polyamide tube (10') was prepared in the same manner as in Example 1 except that the coating liquid (10') prepared above was used instead of the coating liquid (1') in Example 1. Here, a mixing ratio (weight ratio) of polyacrylamide to the hydrophilic copolymer (2) in the surface lubricious layer of the polyamide tube (10') is 1:10.

Next, the obtained polyamide tube (10') was evaluated for the lubricating property (the sliding resistance value at the first reciprocation) in the same manner as in Example 1 and according to the same evaluation criteria, and a result thereof was

Example 11

An acrylamide-acrylic acid-sodium acrylate copolymer (manufactured by Sigma-Aldrich Co. LLC., product name: [poly(acrylamide-co-acrylic acid) partial sodium salt], number average molecular weight (Mn)=150,000, and acrylamide content=84 mol %) was dissolved in water so as to be 0.1 wt % and the copolymer (A) obtained in Production Example 1 (corresponding to the hydrophilic copolymer (2) according to the disclosure) was dissolved in water so as to be 1 wt %, to prepare a coating liquid (11'). A mixing ratio (weight ratio) of the acrylamide-acrylic acid-sodium acrylate copolymer to the hydrophilic copolymer (2) in the coating liquid (11') is 1:10.

A polyamide tube (11') was prepared in the same manner as in Example 1 except that the coating liquid (11') prepared above was used instead of the coating liquid (1') in Example 1. Here, a mixing ratio (weight ratio) of the acrylamide-sodium acrylate copolymer to the hydrophilic copolymer (2) in the surface lubricious layer of the polyamide tube (11') is 1:10.

Next, the obtained polyamide tube (11') was evaluated for the lubricating property (the sliding resistance value at the first reciprocation) in the same manner as in Example 1 and according to the same evaluation criteria, and a result thereof was "B".

Example 12

The copolymer (B) obtained in Production Example 2 (corresponding to the hydrophilic copolymer (1) according to the disclosure) was dissolved in ethanol/water (3/7 w/w) so as to be 10 wt %, to prepare a coating liquid (1-B). Next, a polyamide tube (having an outer diameter of 2.4 mm and a length of 70 mm) was dipped in the coating liquid (1-B), and was taken out at a rate of 1 mm/sec. Next, the polyamide tube was dried at room temperature for 60 seconds to remove the solvent. Next, the polyamide tube was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form an adhesive layer on the polyamide tube (polyamide tube (1-B)). Note that as a UV irradiation device, ECE2000 (high pressure mercury lamp) manufactured by Dymax Corporation was used.

Next, polyacrylamide manufactured by Sigma-Aldrich Co. LLC. (number average molecular weight (Mn)=150,000) was dissolved in water so as to be 0.1 wt % and the copolymer (B) obtained in Production Example 2 (corresponding to the hydrophilic copolymer (2) according to the disclosure) was dissolved in water so as to be 1 wt %, to prepare a coating liquid (12'). A mixing ratio (weight ratio) of polyacrylamide to the hydrophilic copolymer (2) in the coating liquid (12') is 1:10. Next, the polyamide tube (1-B) prepared above was dipped in the coating liquid (12') and was taken out at a rate of 5 mm/sec. Next, the polyamide tube (1-B) was dried at room temperature for 60 seconds to remove the solvent. Next, the polyamide tube (1-B) was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form a surface lubricious layer on the adhesive layer of the polyamide tube (1-B) (polyamide tube (12')). Note that as a UV irradiation device, ECE2000 (high pressure mercury lamp) manufactured by Dymax Corporation was used. A mixing ratio (weight ratio) of polyacrylamide to the hydrophilic copolymer (2) in the surface lubricious layer of the polyamide tube (12') is 1:10.

Next, the obtained polyamide tube (12') was evaluated for the lubricating property (the sliding resistance value at the first reciprocation) in the same manner as in Example 1 and according to the same evaluation criteria, and a result thereof was "A".

Example 13

Polyacrylamide manufactured by Sigma-Aldrich Co. LLC. (number average molecular weight (Mn)=150,000) was dissolved in water so as to be 0.1 wt % and the copolymer (B) obtained in Production Example 2 (corresponding to the hydrophilic copolymer (2) according to the disclosure) was dissolved in water so as to be 1 wt %, to prepare a coating liquid (13'). A mixing ratio (weight ratio) of polyacrylamide to the hydrophilic copolymer (2) in the coating liquid (13') is 1:10.

A polyamide tube (13') was prepared in the same manner as in Example 1 except that the coating liquid (13') prepared as above was used instead of the coating liquid (1') in Example 1. Here, a mixing ratio (weight ratio) of polyacrylamide to the hydrophilic copolymer (2) in the surface lubricious layer of the polyamide tube (13') is 1:10.

Next, the obtained polyamide tube (13') was evaluated for the lubricating property (the sliding resistance value at the first reciprocation) in the same manner as in Example 1 and according to the same evaluation criteria, and a result thereof was "A".

Example 14

Polyacrylamide manufactured by Sigma-Aldrich Co. LLC. (number average molecular weight (Mn)=150,000) was dissolved in water so as to be 0.1 wt % and the copolymer (A) obtained in Production Example 1 (corresponding to the hydrophilic copolymer (2) according to the disclosure) was dissolved in water so as to be 1 wt %, to prepare a coating liquid (14'). A mixing ratio (weight ratio) of polyacrylamide to the hydrophilic copolymer (2) in the coating liquid (14') is 1:10.

A polyamide tube (14') was prepared in the same manner as in Example 12 except that the coating liquid (14') prepared as above was used instead of the coating liquid (12') in Example 12. Here, a mixing ratio (weight ratio) of polyacrylamide to the hydrophilic copolymer (2) in the surface lubricious layer of the polyamide tube (14') is 1:10.

Next, the obtained polyamide tube (14') was evaluated for the lubricating property (the sliding resistance value at the first reciprocation) in the same manner as in Example 1 and according to the same evaluation criteria, and a result thereof was "A".

Example 15

The copolymer (A) obtained in Production Example 1 (corresponding to the hydrophilic copolymer (1) according to the disclosure) was dissolved in ethanol/water (3/7 w/w) so as to be 7 wt %, to prepare a coating liquid (1-C). Next, a polyamide tube (having an outer diameter of 2.4 mm and a length of 70 mm) was dipped in the coating liquid (1-C), and was taken out at a rate of 1 mm/sec. Next, the polyamide tube was dried at room temperature for 60 seconds to remove the solvent. Next, the polyamide tube was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form an adhesive layer on the polyamide tube (polyamide tube (1-C)). Note that as a UV irradiation device, ECE2000 (high pressure mercury lamp) manufactured by Dymax Corporation was used.

Next, polyacrylamide manufactured by Sigma-Aldrich Co. LLC. (number average molecular weight (Mn)=150,000) was dissolved in water so as to be 0.1 wt % and the copolymer (A) obtained in Production Example 1 (corresponding to the hydrophilic copolymer (2) according to the disclosure) was dissolved in water so as to be 1 wt %, to prepare a coating liquid (15'). A mixing ratio (weight ratio) of polyacrylamide to the hydrophilic copolymer (2) in the coating liquid (15') is 1:10. Next, the polyamide tube (1-C) prepared above was dipped in the coating liquid (15') and was taken out at a rate of 5 mm/sec. Next, the polyamide tube (1-C) was dried at room temperature for 60 seconds to remove the solvent. Next, the polyamide tube (1-C) was irradiated with ultraviolet rays (UV) having a wavelength of 365 nm and an irradiation output of 105 $mW/cm^2$ under conditions of an irradiation distance of 250 mm and a sample rotation rate of 3 mm/sec for 3 minutes, so as to form a surface lubricious layer on the adhesive layer of the polyamide tube (1-C) (polyamide tube (15')). Note that as a UV irradiation device, ECE2000 (high pressure mercury lamp) manufactured by Dymax Corporation was used. A mixing ratio (weight ratio) of polyacrylamide to the hydrophilic copolymer (2) in the surface lubricious layer of the polyamide tube (15') is 1:10.

Next, the obtained polyamide tube (15') was evaluated for the lubricating property (the sliding resistance value at the first reciprocation) in the same manner as in Example 1 and according to the same evaluation criteria, and a result thereof was "A".

The results of the above Examples and Comparative Examples are summarized in the following Table 3. Note that in the following Table 3, the mixing ratio indicates a weight ratio of hydrophilic copolymeracrylamide-based polymer in the surface lubricious layer. Columns for each hydrophilic copolymer and each acrylamide-based polymer indicate a concentration of each hydrophilic copolymer and each acrylamide-based polymer in the coating liquid, and the lubricating property means the lubricating property (the sliding resistance value at the first reciprocation).

TABLE 3

| | Adhesive Layer | Surface lubricious layer | | | Lubri- |
|---|---|---|---|---|---|
| | Hydrophilic copolymer (A) | Hydrophilic copolymer (A) | Poly-acrylamide | Mixing weight ratio | cating prop-erty |
| Example 1 | 10 | 1 wt % | 0.1 wt % | 10:1 | A |
| Example 2 | 10 | 5 wt % | 0.1 wt % | 50:1 | C |
| Example 3 | 10 | 2.5 wt % | 0.1 wt % | 25:1 | B |
| Example 4 | 10 | 0.5 wt % | 0.1 wt % | 5:1 | A |
| Example 5 | 10 | 0.1 wt % | 0.1 wt % | 1:1 | B to A |
| Example 6 | 10 | 0.05 wt % | 0.1 wt % | 0.5:1 | C |
| Example 7 | 10 | 1 wt % | 0.01 wt % | 100:1 | C |
| Example 8 | 10 | 1 wt % | 0.05 wt % | 20:1 | A |
| Example 9 | 10 | 1 wt % | 1 wt % | 1:1 | B |

TABLE 3-continued

| | Adhesive Layer | Surface lubricious layer | | | Lubri- |
|---|---|---|---|---|---|
| | Hydrophilic copolymer (A) | Hydrophilic copolymer (A) | Poly-acrylamide | Mixing weight ratio | cating property |
| Comparative Example 1 | 10 | — | — | — | D |
| Example 10 | 10 | 1 wt % | 0.1 wt % | 10:1 | A |
| | Hydrophilic copolymer (A) | Hydrophilic copolymer (A) | Poly (acrylamide-sodium acylate sodium) | Mixing weight ratio | Lubricating property |
| Example 11 | 10 | 1 wt % | 0.1 wt % | 10:1 | B |
| | Hydrophilic copolymer (B) | Hydrophilic copolymer (B) | Poly-acrylamide | Mixing weight ratio | Lubricating property |
| Example 12 | 10 | 1 wt % | 0.1 wt % | 10:1 | A |
| | Hydrophilic copolymer (A) | Hydrophilic copolymer (B) | Poly-acrylamide | Mixing weight ratio | Lubricating property |
| Example 13 | 10 | 1 wt % | 0.1 wt % | 10:1 | A |
| | Hydrophilic copolymer (B) | Hydrophilic copolymer (A) | Poly-acrylamide | Mixing weight ratio | Lubricating property |
| Example 14 | 10 | 1 wt % | 0.1 wt % | 10:1 | A |
| | Hydrophilic copolymer (A) | Hydrophilic copolymer (A) | Poly-acrylamide | Mixing weight ratio | Lubricating property |
| Example 15 | 7 | 1 wt % | 0.1 wt % | 10:1 | A |

What is claimed is:

1. A medical device configured to be positioned in a lumen in a living body, the medical device comprising:

a substrate layer;

an adhesive layer formed on at least a part of the substrate layer, the adhesive layer having a total composition containing a hydrophilic copolymer (1) containing (i) a structural unit derived from a polymerizable monomer (A) having a sulfobetaine structure, (ii) a structural unit derived from a polymerizable monomer (B) having at least one group selected from the group consisting of a sulfonic acid group, a sulfuric acid group, a sulfurous acid group, and salt groups thereof, and (iii) a structural unit derived from a polymerizable monomer (C) having a photoreactive group; and a surface lubricious layer that, due to retained aqueous liquid on the surface lubricious layer, forms a hydrated layer between an inner surface of the lumen and the medical device when the medical device is brought into contact with aqueous liquid in the lumen in the living body, the surface lubricious layer being formed on at least a part of the adhesive layer and being immobilized on the substrate layer by way of the adhesive layer, the surface lubricious layer having a total composition that differs from the total composition of the adhesive layer, the surface lubricious layer containing a polymer, said polymer containing (a) a structural unit derived from acrylamide that retains the aqueous liquid on the surface lubricious layer, and (b) a hydrophilic copolymer (2) containing (i) a structural unit derived from a polymerizable monomer (A') having a sulfobetaine structure, (ii) a structural unit derived from a polymerizable monomer (B') having at least one group selected from the group consisting of a sulfonic acid group, a sulfuric acid group, a sulfurous acid group, and salt groups thereof, and (iii) a structural unit derived from a polymerizable monomer (C') having a photoreactive group.

2. The medical device according to claim 1, wherein the hydrophilic copolymer (2) is contained in the surface lubricious layer at a ratio of more than 0.5 parts by weight and less than 50 parts by weight with respect to 1 part by weight of the polymer containing the structural unit derived from acrylamide.

3. The medical device according to claim 1, wherein the polymer containing the structural unit derived from acrylamide is polyacrylamide.

4. The medical device according to claim 1, wherein the polymerizable monomer (A) and/or (A') is a compound represented by the following formula (1):

[Chem. 1]

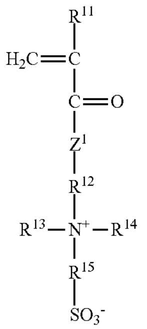

(1)

in the above formula (1), $R^{11}$ represents a hydrogen atom or a methyl group, $Z^1$ represents an oxygen atom or —NH—, $R^{12}$ and $R^{15}$ each independently represent a linear or branched alkylene group having 1 to 20 carbon atoms, and $R^{13}$ and $R^{14}$ each independently represent a linear or branched alkyl group having 1 to 20 carbon atoms.

5. The medical device according to claim 1, wherein the polymerizable monomer (B) and/or (B') is a compound represented by the following formula (2), (3), or (4):

[Chem. 2]

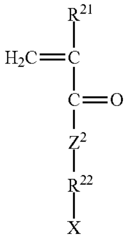

(2)

in the above formula (2), $R^{21}$ represents a hydrogen atom or a methyl group, $Z^2$ represents an oxygen atom or —NH—, $R^{22}$ represents a linear or branched alkylene group having 1 to 20 carbon atoms, and X represents a group selected from the group consisting of a sulfonic acid group ($—SO_3H$), a sulfuric acid group ($—OSO_3H$), a sulfurous acid group ($—OSO_2H$), and salt groups thereof,

[Chem. 3]

(3)

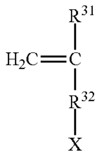

in the above formula (3),
$R^{31}$ represents a hydrogen atom or a methyl group,
$R^{32}$ represents a single bond or a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof, and

[Chem. 4]

(4)

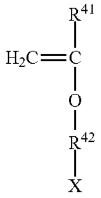

in the above formula (4),
$R^{41}$ represents a hydrogen atom or a methyl group,
$R^{42}$ represents a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof.

6. The medical device according to claim 1, wherein the polymerizable monomer (C) and/or (C') has a group having a benzophenone structure.

7. The medical device according to claim 1, wherein the hydrophilic copolymer (1) and the hydrophilic copolymer (2) have the same structure.

8. The medical device according to claim 1, wherein the medical device is a catheter, a stent, or a guide wire.

9. The medical device according to claim 1, wherein the polymerizable monomer (A) and/or (A') is a compound represented by the following formula (1):

[Chem. 1]

(1)

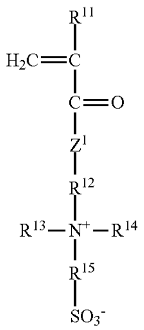

in the above formula (1),
$R^{11}$ represents a hydrogen atom or a methyl group,
$Z^1$ represents an oxygen atom or —NH—,
$R^{12}$ and $R^{15}$ each independently represent a linear or branched alkylene group having 1 to 20 carbon atoms, and
$R^{13}$ and $R^{14}$ each independently represent a linear or branched alkyl group having 1 to 20 carbon atoms;
and wherein the polymerizable monomer (B) and/or (B') is a compound represented by the following formula (2), (3), or (4):

[Chem. 2]

(2)

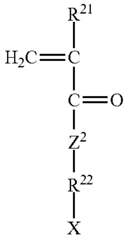

in the above formula (2),
$R^{21}$ represents a hydrogen atom or a methyl group,
$Z^2$ represents an oxygen atom or —NH—,
$R^{22}$ represents a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof,

[Chem. 3]

(3)

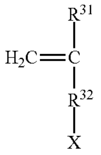

in the above formula (3),
$R^{31}$ represents a hydrogen atom or a methyl group,
$R^{32}$ represents a single bond or a linear or branched alkylene group having 1 to 20 carbon atoms, and
X represents a group selected from the group consisting of a sulfonic acid group ($—SO_3H$), a sulfuric acid group ($—OSO_3H$), a sulfurous acid group ($—OSO_2H$), and salt groups thereof, and

[Chem. 4]

(4)

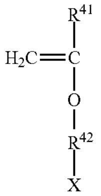

in the above formula (4), $R^{41}$ represents a hydrogen atom or a methyl group, $R^{42}$ represents a linear or branched alkylene group having 1 to 20 carbon atoms, and X represents a group selected from the group consisting of a sulfonic acid group ($-SO_3H$), a sulfuric acid group ($-OSO_3H$), a sulfurous acid group ($-OSO_2H$), and salt groups thereof.

10. The medical device according to claim 9, wherein the polymerizable monomer (C) and/or (C') has a group having a benzophenone structure.

11. The medical device according to claim 9, wherein the hydrophilic copolymer (1) and the hydrophilic copolymer (2) have the same structure.

12. The medical device according to claim 9, wherein the medical device is a catheter, a stent, or a guide wire.

* * * * *